United States Patent
Einav

(10) Patent No.: US 8,915,871 B2
(45) Date of Patent: Dec. 23, 2014

(54) METHODS AND APPARATUSES FOR REHABILITATION EXERCISE AND TRAINING

(75) Inventor: Omer Einav, Emek Hefer (IL)

(73) Assignee: Motorika Limited, Hamilton (BM)

( * ) Notice: Subject to any disclaimer, the term of this patent is extended or adjusted under 35 U.S.C. 154(b) by 1662 days.

(21) Appl. No.: 10/597,605

(22) PCT Filed: Feb. 4, 2005

(86) PCT No.: PCT/IL2005/000136
§ 371 (c)(1),
(2), (4) Date: Jun. 3, 2008

(87) PCT Pub. No.: WO2005/074369
PCT Pub. Date: Aug. 18, 2005

(65) Prior Publication Data
US 2008/0242521 A1    Oct. 2, 2008

Related U.S. Application Data

(60) Provisional application No. 60/542,022, filed on Feb. 5, 2004, provisional application No. 60/566,079, filed (Continued)

(51) Int. Cl.
*A61H 1/02*    (2006.01)
(Continued)

(52) U.S. Cl.
CPC ........... *G06F 19/3481* (2013.01); *A61B 5/4528* (2013.01); *A61B 5/6887* (2013.01);
(Continued)

(58) Field of Classification Search
CPC ......... A61H 1/00; A61H 1/001; A61H 1/003; A61H 1/005; A61H 1/02–1/0296; A61H 2001/02–2001/027; A63B 21/00178; A63B 21/00181; A63B 21/00185; A63B 21/002; A63B 21/0023; A63B 22/0087; A63B 22/0089; A63B 22/14; A63B 22/16; A63B 22/18; A63B 24/00–24/0087; A63B 26/003; A47C 3/18
USPC ........... 601/5, 23–40; 600/595; 482/142–147; 434/247–261; 273/449, 450
See application file for complete search history.

(56) References Cited

U.S. PATENT DOCUMENTS 3,745,990 A * 7/1973 Neis .............................. 600/595
3,824,991 A * 7/1974 Whitaker ......................... 601/5
(Continued)

FOREIGN PATENT DOCUMENTS

DE    10133572    4/2002
EP    0304538     3/1989
(Continued)

OTHER PUBLICATIONS

Translation of Notification of Reason for Rejection Dated Aug. 13, 2010 From the Japanese Patent Office Re. Application No. 2006-552009.

(Continued)

*Primary Examiner* — Valerie L Skorupa

(57) ABSTRACT

A rehabilitation chair system, comprising: a seat adapted for sitting of a human thereon; at least one extender adapted to move relative to said seat; at least one sensor which generates an indication of a balance state of said human; and a controller configured to move said extender while measuring said balance state using said at least one sensor.

40 Claims, 17 Drawing Sheets

Related U.S. Application Data on Apr. 29, 2004, provisional application No. 60/633,429, filed on Dec. 7, 2004, provisional application No. 60/633,442, filed on Dec. 7, 2004, provisional application No. 60/633,428, filed on Dec. 7, 2004.

(51) Int. Cl.

| | | |
|---|---|---|
| *A61H 1/00* | (2006.01) | |
| *A61B 5/11* | (2006.01) | |
| *G06F 19/00* | (2011.01) | |
| *A63B 26/00* | (2006.01) | |
| *A61B 5/103* | (2006.01) | |
| *A63B 71/00* | (2006.01) | |
| *A61B 5/00* | (2006.01) | |
| *A61B 5/0488* | (2006.01) | |

(52) U.S. Cl.
CPC ...... *A63B 2208/0233* (2013.01); *A61B 5/1116* (2013.01); *A61B 2505/09* (2013.01); *A61B 5/6891* (2013.01); *A63B 26/003* (2013.01); *A61B 5/103* (2013.01); *A61B 5/04884* (2013.01); *A61B 5/4519* (2013.01); *A61B 5/702* (2013.01); *A63B 71/0009* (2013.01); *A63B 2071/0018* (2013.01)
USPC ......... 601/5; 601/24; 601/26; 601/33; 601/34

(56) References Cited

U.S. PATENT DOCUMENTS

| | | | |
|---|---|---|---|
| 3,919,691 A | | 11/1975 | Noll |
| 3,929,462 A | | 12/1975 | Karmin |
| 4,099,697 A | * | 7/1978 | Von Schuckmann ......... 248/604 |
| 4,499,900 A | | 2/1985 | Petrofsky et al. |
| 4,582,049 A | | 4/1986 | Ylvisaker |
| 4,685,928 A | | 8/1987 | Yaeger |
| 4,691,694 A | * | 9/1987 | Boyd et al. ....................... 601/34 |
| 4,724,842 A | | 2/1988 | Charters et al. |
| 4,765,610 A | | 8/1988 | Sidwell |
| 4,773,398 A | | 9/1988 | Tatom |
| 4,824,104 A | | 4/1989 | Bloch |
| 4,883,067 A | | 11/1989 | Knispel et al. |
| 4,921,244 A | | 5/1990 | Berroth |
| 4,936,299 A | | 6/1990 | Erlandson |
| 4,966,413 A | * | 10/1990 | Palarski ......................... 297/330 |
| 5,048,826 A | | 9/1991 | Ryan |
| 5,070,873 A | | 12/1991 | Graupe et al. |
| 5,158,074 A | * | 10/1992 | Grellas ............................ 601/24 |
| 5,179,939 A | * | 1/1993 | Donovan et al. ................. 601/33 |
| 5,193,539 A | | 3/1993 | Schulman et al. |
| 5,193,540 A | | 3/1993 | Schulman et al. |
| 5,201,772 A | | 4/1993 | Maxwell |
| 5,211,161 A | | 5/1993 | Stef |
| 5,231,998 A | | 8/1993 | Rosen et al. |
| 5,244,441 A | | 9/1993 | Dempster et al. |
| 5,269,318 A | * | 12/1993 | Nashner ........................ 600/595 |
| 5,282,460 A | | 2/1994 | Boldt |
| 5,311,880 A | * | 5/1994 | Lancaster et al. ............. 600/595 |
| 5,312,439 A | | 5/1994 | Loeb |
| 5,324,316 A | | 6/1994 | Schulman et al. |
| 5,343,856 A | | 9/1994 | Proctor |
| 5,358,251 A | * | 10/1994 | Ashton ......................... 473/269 |
| 5,391,128 A | | 2/1995 | DeBear |
| 5,397,865 A | | 3/1995 | Park |
| 5,405,367 A | | 4/1995 | Schulman et al. |
| 5,411,044 A | * | 5/1995 | Andolfi ............................ 135/66 |
| 5,413,611 A | | 5/1995 | Haslam, II et al. |
| 5,454,774 A | | 10/1995 | Davis |
| 5,466,213 A | * | 11/1995 | Hogan et al. .................... 601/33 |
| 5,476,103 A | | 12/1995 | Nahsner |
| 5,476,428 A | | 12/1995 | Potash et al. |
| 5,616,104 A | | 4/1997 | Mulenburg et al. |
| 5,662,693 A | | 9/1997 | Johnson et al. |
| 5,690,389 A | | 11/1997 | Ekman et al. |
| 5,755,645 A | | 5/1998 | Miller et al. |
| 5,830,160 A | | 11/1998 | Reinkensmeyer |
| 5,836,304 A | | 11/1998 | Kellinger et al. |
| 5,846,086 A | | 12/1998 | Bizzi et al. |
| 5,853,353 A | | 12/1998 | Blümel |
| 5,919,115 A | | 7/1999 | Horowitz et al. |
| 5,954,621 A | | 9/1999 | Joutras et al. |
| 5,980,435 A | | 11/1999 | Joutras et al. |
| 6,004,244 A | | 12/1999 | Simonson |
| 6,035,465 A | | 3/2000 | Rogozinski |
| 6,051,017 A | | 4/2000 | Loeb et al. |
| 6,057,828 A | | 5/2000 | Rosenberg et al. |
| 6,061,004 A | | 5/2000 | Rosenberg et al. |
| 6,064,912 A | | 5/2000 | Kenney |
| 6,246,200 B1 | | 6/2001 | Blumenkranz et al. |
| 6,270,445 B1 | | 8/2001 | Dean, Jr. et al. |
| 6,354,945 B1 | | 3/2002 | Furuki et al. |
| 6,379,393 B1 | | 4/2002 | Mavroidis et al. |
| 6,478,721 B1 | | 11/2002 | Hunter |
| 6,558,304 B1 | * | 5/2003 | Bardon et al. ................. 482/147 |
| 6,592,315 B2 | | 7/2003 | Osborne, Jr. |
| 6,613,000 B1 | | 9/2003 | Reinkensmeyer et al. |
| 6,645,126 B1 | | 11/2003 | Martin et al. |
| 6,682,351 B1 | * | 1/2004 | Abraham-Fuchs et al. .. 434/247 |
| 6,774,885 B1 | | 8/2004 | Even-Zohar |
| 6,829,510 B2 | | 12/2004 | Nathan et al. |
| 6,839,594 B2 | | 1/2005 | Cohen et al. |
| 6,966,882 B2 | | 11/2005 | Horst |
| 7,115,078 B1 | * | 10/2006 | Kalember et al. ............ 482/117 |
| 7,163,488 B2 | | 1/2007 | Anders et al. |
| 7,209,788 B2 | | 4/2007 | Nicolelis et al. |
| 7,381,192 B2 | | 6/2008 | Brodard et al. |
| 7,504,577 B2 | | 3/2009 | Riopelle |
| 8,012,107 B2 | | 9/2011 | Einav et al. |
| 2002/0064438 A1 | | 5/2002 | Osborne, Jr. |
| 2002/0094913 A1 | | 7/2002 | Valentino |
| 2003/0032524 A1 | | 2/2003 | Lamar et al. |
| 2003/0199370 A1 | | 10/2003 | Bucay-Bissu |
| 2003/0208109 A1 | | 11/2003 | David et al. |
| 2003/0208246 A1 | | 11/2003 | Kotlik et al. |
| 2004/0102723 A1 | | 5/2004 | Horst |
| 2004/0106881 A1 | | 6/2004 | McBean et al. |
| 2004/0172097 A1 | | 9/2004 | Brodard et al. |
| 2004/0180768 A1 | | 9/2004 | Almada |
| 2004/0245838 A1 | | 12/2004 | Chiu |
| 2005/0261114 A1 | | 11/2005 | Heitzman et al. |
| 2006/0149338 A1 | | 7/2006 | Flaherty et al. |
| 2006/0167564 A1 | | 7/2006 | Flaherty et al. |
| 2006/0229164 A1 | | 10/2006 | Einav |
| 2006/0277074 A1 | | 12/2006 | Einav et al. |
| 2006/0293617 A1 | | 12/2006 | Einav et al. |
| 2007/0282228 A1 | | 12/2007 | Einav et al. |
| 2007/0299371 A1 | | 12/2007 | Einav et al. |
| 2008/0132383 A1 | | 6/2008 | Einav et al. |
| 2008/0161733 A1 | | 7/2008 | Einav et al. |

FOREIGN PATENT DOCUMENTS

| | | |
|---|---|---|
| EP | 0569489 | 11/1993 |
| EP | 0703752 | 4/1996 |
| EP | 0862930 | 9/1998 |
| EP | 1145682 | 10/2001 |
| EP | 1364636 | 11/2003 |
| FR | 2809615 | 12/2001 |
| GB | 2357848 | 7/2011 |
| JP | 59-160455 | 9/1984 |
| JP | 60-200312 | 10/1985 |
| JP | 61-071984 | 4/1986 |
| JP | 61-217174 | 9/1986 |
| JP | 61-265151 | 11/1986 |
| JP | 01-316815 | 12/1989 |
| JP | 02-102652 | 4/1990 |
| JP | 05-007608 | 1/1993 |
| JP | 05-026209 | 4/1993 |
| JP | 06-505407 | 6/1994 |
| JP | 07-163626 | 6/1995 |
| JP | 08-322189 | 12/1996 |
| JP | 08-511448 | 12/1996 |

(56) References Cited

FOREIGN PATENT DOCUMENTS

| | | |
|---|---|---|
| JP | 03-039345 | 4/1997 |
| JP | 09-173499 | 7/1997 |
| JP | 3044600 | 10/1997 |
| JP | 3048540 | 2/1998 |
| JP | 10-207624 | 8/1998 |
| JP | 11-009574 | 1/1999 |
| JP | 11-155836 | 6/1999 |
| JP | 11-253504 | 9/1999 |
| JP | 2000-102523 | 4/2000 |
| JP | 2000-112335 | 4/2000 |
| JP | 2000-102523 | 10/2000 |
| JP | 2000-279463 | 10/2000 |
| JP | 3126901 | 11/2000 |
| JP | 2001-204850 | 7/2001 |
| JP | 3081786 | 8/2001 |
| JP | 2001-299842 | 10/2001 |
| JP | 2002-065891 | 3/2002 |
| JP | 2002-126019 | 5/2002 |
| JP | 2002-127058 | 5/2002 |
| JP | 3087629 | 5/2002 |
| JP | 2002-263213 | 9/2002 |
| JP | 2002-351993 | 12/2002 |
| JP | 2003-093451 | 4/2003 |
| JP | 2003-164544 | 6/2003 |
| JP | 2003-190235 | 7/2003 |
| JP | 2004-008751 | 1/2004 |
| JP | 2004-174692 | 6/2004 |
| WO | WO 92/13504 | 8/1992 |
| WO | WO 98/37926 | 9/1998 |
| WO | WO 98/43700 | 10/1998 |
| WO | WO 98/43701 | 10/1998 |
| WO | WO 98/46127 | 10/1998 |
| WO | WO 02/13673 | 2/2002 |
| WO | WO 02/35457 | 5/2002 |
| WO | WO 02/092164 | 11/2002 |
| WO | WO 03/023546 | 3/2003 |
| WO | WO 2004/050172 | 6/2004 |
| WO | WO 2005/074369 | 8/2005 |
| WO | WO 2005/074370 | 8/2005 |
| WO | WO 2005/074371 | 8/2005 |
| WO | WO 2005/074372 | 8/2005 |
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2005/105203 | 11/2005 |
| WO | WO 2006/021952 | 3/2006 |
| WO | WO 2006/061834 | 6/2006 |
| WO | WO 2006/082584 | 8/2006 |
| WO | WO 2006/82584 | 8/2006 |

OTHER PUBLICATIONS

Translation of Notification of Reasons of Rejection Dated Jun. 12, 2009 From the Japanese Patent Office Re.: Application No. 2006-552011.
Translation of Notification of Reasons of Rejection Dated Sep. 14, 2009 From the Japanese Patent Office Re.: Application No. 2006-552014.
Translation of Notification of Reasons for Rejection Dated Dec. 15, 2010 From the Japanese Patent Office Re. Application No. 2009-027772.
Communication Pursuant to Article 96(2) Dated Dec. 11, 2006 From the European Patent Office Re.: Application No. 05703180.9.
Examination Report Dated Oct. 23, 2008 From the Instituto Mexicano de la Propriedad Industrial Re.: Application No. PA/a/2006/008919.
Examination Report Dated Oct. 29, 2008 From the Instituto Mexicano de la Propriedad Industrial Re.: Application No. PA/a2006/008914.
International Preliminary Report on Patentability Dated Aug. 16, 2007 From the International Bureau of WIPO Re.: Application No. PCT/IL2006/000140.
International Preliminary Report on Patentability Dated Jan. 19, 2007 From the International Preliminary Examining Authority Re.: Application No. PCT/IL05/00138.
International Preliminary Report on Patentability Dated Apr. 26, 2007 From the International Bureau of WIPO Re.: Application No. PCT/IL2005/000139.
International Preliminary Report on Patentability Dated Sep. 29, 2008 From the International Preliminary Examining Authority Re.: Application No. PCT/IL06/00140.
International Search Report and the Written Opinion Dated Jan. 3, 2007 From the International Searching Authority Re.: Application No. PCT/IL06/00140.
Office Action Dated Sep. 26, 2008 From the State Intellectual Properety Office of the People's Republic of China Re.: Application No. 20580010391.4.
Official Action Dated Oct. 1, 2008 From the US Patent and Trademark Office Re.: U.S. Appl. No. 11/389,773.
Communication of Results From Examination Dated Oct. 23, 2008 From the Instituto Mexicano de la Propriedad Industrial Re.: Application No. PA/a/2006/008914 and Its Translation into English.
Communication Pursuant to Article 94(3) EPC Dated Oct. 12, 2009 From the European Patent Office Re.: Application No. 06704564.1.
International Preliminary Report on Patentability Dated Mar. 8, 2007 From the International Bureau of WIPO Re.: Application No. PCT/IL2005/000906.
International Preliminary Report on Patentability Dated Jun. 12, 2006 From the International Preliminary Examining Authority Re.: Application No. PCT/IL2005/000442.
International Preliminary Report on Patentability Dated Aug. 17, 2006 From the International Bureau of WIPO Re.: Application No. PCT/IL2005/000136.
International Preliminary Report on Patentability Dated Aug. 17, 2006 From the International Bureau of WIPO Re.: Application No. PCT/IL2005/000140.
International Preliminary Report on Patentability Dated Aug. 17, 2006 From the International Bureau of WIPO Re.: Application No. PCT/IL2005/000141.
International Preliminary Report on Patentability Dated Jun. 21, 2007 From the International Bureau of WIPO Re.: Application No. PCT/IL2005/001318.
Notification of Reasons of Rejection Dated Jun. 4, 2009 From the Japanese Patent Office Re.: Application No. 2006-552011.
Notification of Reasons of Rejection Dated Sep. 14, 2009 From the Japanese Patent Office Re.: Application No. 2006-552015 and Its Translation Into English.
Official Action Dated Dec. 18, 2009 From the US Patent and Trademark Office Re.: U.S. Appl. No. 11/348,128.
Official Action Dated Mar. 19, 2010 From the US Patent and Trademark Office Re.: U.S. Appl. No. 10/597,675.
Official Action Dated May 19, 2009 From the US Patent and Trademark Office Re.: U.S. Appl. No. 11/792,477.
Official Action Dated Oct. 23, 2008 From the Instituto Mexicano de la Propriedad Industrial, Divisional Direction of Patents Re.: Application No. PA/a/2006/008919 and Its Translation Into English.
Official Action Dated Jun. 24, 2009 From the US Patent and Trademark Office Re.: U.S. Appl. No. 11/207,655.
Response Dated Feb. 7, 2010 to Notification of Reasons of Rejection Dated Sep. 14, 2009 From the Japanese Patent Office Re.: Application No. 2006-552015.
Response Dated Feb. 9, 2010 to Notification of Reasons of Rejection of Sep. 14, 2009 From the Japanese Patent Office Re.: Application No. 2006-552014.
Response Dated Apr. 13, 2010 to Communication Pursuant to Article 94(3) EPC of Oct. 12, 2009 From the European Patent Office Re.: Application No. 06704564.1.
Translation of Office Action Dated Jan. 21, 2009 From the Japanese Patent Office Re.: Application No. 2006-552008.
Response Dated Apr. 19, 2010 to Official Action of Mar. 19, 2010 From the US Patent and Trademark Office Re.: U.S. Appl. No. 10/597,675.
Supplementary Partial European Search Report and the European Search Opinion Dated Jul. 14, 2009 From the European Patent Office Re.: Application No. 06704564.1.

(56) References Cited

OTHER PUBLICATIONS

Response Dated Apr. 6, 2011 to Notification of Reasons for Rejection of Jan. 27, 2011 From the Japanese Patent Office Re. Application No. 2007-510233.
Response Dated Apr. 10, 2011 to Notification of Reasons for Rejection of Dec. 15, 2010 From the Japanese Patent Office Re. Application No. 2009027772.
Pfurtscheller et al. "Brain Oscillations Control Hand Orthosis in a Tetraplegic", Neuroscience Letters, 292: 211-214, 2000.
Official Action Dated May 9, 2011 From the US Patent and Trademark Office Re.: U.S. Appl. No. 11/568,463.
Response Dated May 16, 2011 to Official Action of Mar. 15, 2011 From the US Patent and Trademark Office Re. U.S. Appl. No. 10/597,602.
Proceeding Further With the European Patent Application Pursuant to Rule 70(2) EPC Dated Jul. 31, 2009 From the European Patent Office Re.: Application No. 06704564.1.
Translation of Notification of Reasons of Rejection Dated Mar. 9, 2010 From the Japanese Patent Office Re.: Application No. 2006-552008.
Translation of Notification of Reasons of Rejection Dated Jul. 4, 2011 From the Japanese Patent Office Re. Application No. 2006-552013.
Official Action Dated Jun. 28, 2010 From the US Patent and Trademark Office Re.: U.S. Appl. No. 11/568,463.
Translation of Notification of Reasons of Rejection Dated May 26, 2010 From the Japanese Patent Office Re. Application No. 2006-552013.
Translation of Notice of Reason for Rejection Dated Jun. 4, 2010 From the Japanese Patent Office Re. Application No. 2007-529131.
Examination Report Dated Aug. 25, 2011 From the Government of India, Patent Office Intellectual Property Building Re.: Application No. 3230/CHENP/2006.
Examination Report Dated Aug. 25, 2011 From the Government of India, Patent Office, Intellectual Property Building Re. Application No. 3232/CHENP/2006.
Examination Report Dated Aug. 25, 2011 From the Government of India, Patent Office, Intellectual Property Building Re.: Application No. 3231/CHENP/2006.
Response Dated Aug. 24, 2011 to Notification of Reasons for Rejection of Jun. 6, 2011 From the Japanese Patent Office Re. Application No. 2009-027772.
Notice of Reasons for Rejection Dated Aug. 31, 2011 From the Japanese Patent Office Re. Application No. 2006-552009 and Its Translation Into English.
Response Dated Feb. 22, 2011 to Official Decision of Rejection of Oct. 29, 2010 From the Japanese Patent Office Re. Application No. 2007-529131.
International Preliminary Report on Patentability Dated Apr. 21, 2010 From the International Preliminary Examining Authority Re.: Application No. PCT/IL05/00138.
Official Action Dated Mar. 15, 2011 From the US Patent and Trademark Office Re. U.S. Appl. No. 10/597,602.
Notice of Allowance Dated Feb. 16, 2011 From the US Patent and Trademark Office Re.: U.S. Appl. No. 10/597,675.
Translation of Notification of Reason for Rejection Dated Apr. 7, 2011 From the Japanese Patent Office Re. Application No. 2006-552014.
Translation of Notification of Reasons for Rejection Dated Apr. 6, 2011 From the Japanese Patent Office Re. Application No. 2006-215045.
Official Action Dated Mar. 16, 2011 From the US Patent and Trademark Office Re.: U.S. Appl. No. 11/568,463.
Translation of Questioning Dated May 25, 2011 From the Japanese Patent Office Re. Application No. 2006-552015.
Official Action Dated Jun. 15, 2010 From the US Patent and Trademark Office Re. U.S. Appl. No. 10/597,671.
Translation of Notification of Reasons for Rejection Dated Jun. 6, 2011 From the Japanese Patent Office Re. Application No. 2009-027772.
Official Action Dated Sep. 1, 2011 From the US Patent and Trademark Office Re.: U.S. Appl. No. 11/568,463.
Official Action Dated Sep. 23, 2011 From the US Patent and Trademark Office Re. U.S. Appl. No. 10/597,671.
Response Dated Sep. 26, 2011 to Notification of Reasons of Rejection of Jul. 4, 2011 From the Japanese Patent Office Re. Application No. 2006-552013.
Response Dated Oct. 5, 2011 to Notification of Reason for Rejection of Apr. 7, 2011 From the Japanese Patent Office Re. Application No. 2006-552014.
Official Action Dated Oct. 7, 2011 From the US Patent and Trademark Office Re.: U.S. Appl. No. 11/568,463.
Backlife "The Backlife Idea", Product Information, <http://www.backlife.com>, 27 P., 2003.
Bak "The Complex Motion of Standing Still. Hydraulics, Sensors, and Human Modeling Dsta-Unified by Proprietary Software", <http://www.designnews.com/article/CA73202>, 5 P., 2001.
Burgar et al. "Development of Robots for Rehabilitation Therapy: The Palo Alto VA/Stanford Experience", Journal of Rehabilitation Research and Development, 37(6): 663-673, 2000.
Cameron et al. "Micromodular Implants to Provide Electrical Stimulation of Paralyzed Muscles and Limbs", IEEE Transactions on Biomedical Engineering, 44(9): 781-790, 1997. Abstract.
Graupe "EMG Pattern Analysis for Patient-Responsive Control of FES in Paraplegics for Walker-Supported Walking", IEEE Transactions on Biomedical Engineering, 36(7): 711-719, 1989. p. 711, 1-h Col., Paragraph 1 -r-h Col., Paragraph 1, Figs.3, 5, p. 716, 1-h Col., Figs.
Messinger "ReAbility Games: Island Hunt Catch'em Patrol Muzment", Detailed Specifications Document, NOKs Technologies, Version 1.0, 16 P., 2004.
Micromedical "BalanceQuest: Computerized Dynamic Posturography", Micromedical Technologies, <http://www.micromedial.com>, 6 P., 2001.
Peasgood et al. "EMG-Controlled Dosed Loop Electrical Stimulation Using a Digital Signal Processor", Electronics Letters, 36(22): 1832-1833, 2000. p. 1832, 1-h Col., Paragraph 1, Fig.1, p. 1833, r-h Col., Paragraph 1.
Richardson et al. "Comparing Smooth Arm Movement With the Two-Thirds Power Law and the Related Segmented-Control Hypothesis", The Journal of Neuroscience, 22(18): 8201-8211, 2002.
Viviani et al. "Minimum-Jerk, Two-Thirds Power Law, and Isochrony: Converging Approaches to Movement Planning", Journal of Experimental Psychology: Human Perception and Performance, 17: 32-53, 1995. Abstract.
Viviani et al. "Trajectory Determines Movement Dynamics", The Journal of Neuroscience, 7: 431-437, 1982.
Official Action Dated Nov. 15, 2011 From the US Patent and Trademark Office Re. U.S. Appl. No. 10/597,633.
Response Dated Oct. 17, 2011 to Official Action of Jul. 18, 2011 From the US Patent and Trademark Office Re. U.S. Appl. No. 10/597,602.
International Preliminary Report on Patentability Dated May 11, 2006 From the International Preliminary Examining Authority Re.: Application No. PCT/IL2005/000137.
International Preliminary Report on Patentability Dated Jan. 23, 2006 From the International Preliminary Examining Authority Re.: Application No. PCT/IL2005/000135.
International Search Report and the Written Opinion Dated Sep. 6, 2006 From the International Searching Authority Re.: Application No. PCT/IL05/01318.
International Search Report and the Written Opinion Dated May 12, 2006 From the International Searching Authority Re.: Application No. PCT/IL05/00136.
International Search Report and the Written Opinion Dated Jul. 17, 2006 From the International Searching Authority Re.: Application No. PCT/IL05/00142.
International Search Report Dated Jun. 2, 2005 From the International Searching Authority Re.: Application No. PCT/IL2005/000139.
International Search Report Dated Feb. 3, 2006 From the International Searching Authority Re.: Application No. PCT/IL05/00140.

(56) References Cited

OTHER PUBLICATIONS

International Search Report Dated Jun. 8, 2006 From the International Searching Authority Re.: Application No. PCT/IL05/00906.
International Search Report Dated Nov. 17, 2005 From the International Searching Authority Re.: Application No. PCT/IL2005/000137.
International Search Report Dated Oct. 17, 2005 From the International Searching Authority Re.: Application No. PCT/IL05/00138.
International Search Report Dated Aug. 24, 2005 From the International Searching Authority Re.: Application No. PCT/IL2005/000442.
International Search Report Dated Nov. 28, 2005 From the International Searching Authority Re.: Application No. PCT/IL2005/00141.
International Searching Report Dated Jun. 3, 2005 From the International Searching Authority Re.: Application No. PCT/IL2005/000135.
Official Action Dated Feb. 7, 2008 From the US Patent and Trademark Office Re.: U.S. Appl. No. 11/389,773.
Official Action Dated May 19, 2008 From the US Patent and Trademark Office Re.: U.S. Appl. No. 11/207,655.
Official Action Dated Jul. 26, 2007 From the US Patent and Trademark Office Re.: U.S. Appl. No. 11/389,773.
Official Action Dated Sep. 30, 2008 From the US Patent and Trademark Office Re.: U.S. Appl. No. 11/207,655.
Supplementary Partial European Search Report Dated Jan. 29, 2008 From the European Patent Office Re.: Application No. 05774725.5.
Written Opinion Dated Jun. 2, 2005 From the International Searching Authority Re.: Application No. PCT/IL2005/000139.
Written Opinion Dated Feb. 3, 2006 From the International Searching Authority Re.: Application No. PCT/IL05/00140.
Written Opinion Dated Jun. 3, 2005 From the International Searching Authority Re.: Application No. PCT/IL2005/000135.
Written Opinion Dated Jun. 8, 2006 From the International Searching Authority Re.: Application No. PCT/IL05/00906.
Written Opinion Dated Nov. 17, 2005 From the International Searching Authority Re.: Application No. PCT/IL2005/000137.
Written Opinion Dated Oct. 17, 2005 From the International Searching Authority Re.: Application No. PCT/IL05/00138.
Written Opinion Dated Aug. 24, 2005 From the International Searching Authority Re.: Application No. PCT/IL2005/000442.
Written Opinion Dated Nov. 28, 2005 From the International Searching Authority Re.: Application No. PCT/IL05/00141.
Russo "An Other Reality", Maariv, p. 14, Oct. 26, 2004. Hebrew Only!
Official action dated Sep. 14, 2010 from the US patent and trademark office re. U.S. Appl. No. 10/597,756.
Response dated Sep. 27, 2010 to notification of reasons for rejection of Jul. 12, 2010 from the Japanese patent office re. Application No. 2006-215045.
Response dated Sep. 20, 2010 to notice of reason for rejection of Jun. 4, 2010 from the Japanese patent office re. Application No. 2007-529131.
Response dated Sep. 22, 2010 to notification of reasons of rejection of May 26, 2010 from the Japanese patent office re. Application No. 2006-552013.
Response dated Sep. 26, 2010 to notification of reason for rejection of Jul. 9, 2010 from the Japanese patent office re. Application No. 2006-552014.
Response dated Sep. 27, 2010 to official action of Jun. 28, 2010 from the US patent and trademark office re.: U.S. Appl. No. 11/568,463.
Official Action Dated Dec. 7, 2011 From the US Patent and Trademark Office Re.: U.S. Appl. No. 11/660,965.
Harwin et al. "Clinical Potential and Design of Programmable Mechanical Impedances for Orthotic Applications", Robotica, 16: 523-530, 1998.
Weiskopf et al. "Principles of a Brain-Computer Interface (BCI) Based on Real-Time Functional Magnetic Resonance Imaging (FMRI)", IEEE Transactions on Biomedical Engineering, 51(6): 966-970, Jun. 2004.
Yoo et al. "Drain-Computer Interface Using FMRI: Spatial Navigation by Thoughts", Clinical Neuroescience and Neuropathology, 15(10): 1591-1595, Jul. 19, 2004.
Response Dated Jun. 14, 2011 to Notification of Reason for Rejection of Feb. 3, 2011 From the Japanese Patent Office Re. Application No. 2006-552009.
Translation of Decision of Rejection Dated Jun. 30, 2011 From the Japanese Patent Office Re. Application No. 2007-510233.
Official Action Dated Jul. 7, 2010 From the US Patent and Trademark Office Re.: U.S. Appl. No. 10/597,675.
Translation of Notification of Reason for Rejection Dated Jul. 9, 2010 From the Japanese Patent Office Re. Application No. 2006-552014.
Restriction Official Action Dated Dec. 12, 2011 From the US Patent and Trademark Office Re. U.S. Appl. No. 10/597,635.
Examination Report Dated Oct.23, 2008 From the Instituto Mexicano de la Propriedad Industrial Re.: Application No. PA/a/2006/008919.
Official Action Dated Jun. 15, 2011 From the US Patent and Trademark Office Re. U.S. Appl. No. 10/597,671.
Official Action Dated Dec. 29, 2008 From the US Patent and Trademark Office Re.: U.S. Appl. No. 11/792,477.
Response Dated Jul. 6, 2011 to the Notification of Reasons for Rejection of Apr. 6, 2011 From the Japanese Patent Office Re. Application No. 2006-215045.
Response Dated Jun. 9, 2011 to Official Action of May 9, 2011 From the US Patent and Trademark Office Re.: U.S. Appl. No. 11/568,463.
Response Dated Jul. 12, 2011 to Official Action of Jun. 15, 2011 From the US Patent and Trademark Office Re. U.S. Appl. No. 10/597,671.
Response Dated Jul. 18, 2011 to Official Action of Mar. 16, 2011 From the US Patent and Trademark Office Re.: U.S. Appl. No. 11/568,463.
Official Action Dated Jul. 18, 2011 From the US Patent and Trademark Office Re. U.S. Appl. No. 10/597,602.
Response Dated Aug. 9, 2011 to Questioning of May 25, 2011 From the Japanese Patent Office Re. Application No. 2006-552015.
Response Dated Aug. 4, 2010 to Notification of Reasons of Rejection of Mar. 9, 2010 From the Japanese Patent Office Re.: Application No. 2006-552008.
Translation of Notification of Reasons for Rejection Dated Jul. 12, 2010 From the Japanese Patent Office Re. Application No. 2006-215045.
Official Action Dated Aug. 10, 2011 From the US Patent and Trademark Office Re. U.S. Appl. No. 10/597,633.
Official Action Dated Sep. 1, 2011 From the US Patent and Trademark Office Re.: U.S. Appl. No. 11/660,965.
Response Dated Nov. 9, 2011 to Notice of Reasons for Rejection of Aug. 31, 2011 From the Japanese Patent Office Re. Application No. 2006-552009.
Response Dated Nov. 1, 2010 to Decision of Rejection of Jul. 9, 2010 From the Japanese Patent Office Re. Application No. 2006-552015.
Response Dated Dec. 6, 2010 to Official Action of Jul. 7, 2010 From the US Patent and Trademark Office Re.: U.S. Appl. No. 10/597,675.
Translation of Decision of Rejection Dated Jul. 9, 2010 From the Japanese Patent Office Re. Application No. 2006-552015.
Translation of Official Decision of Rejection Dated Oct. 29, 2010 From the Japanese Patent Office Re. Application No. 2007-529131.
Response Dated Dec. 1, 2011 to Official Action of Sep. 1, 2011 From the US Patent and Trademark Office Re.: U.S. Appl. No. 11/883,663.
Translation of Decision of Rejection Dated Feb. 1, 2011 From the Japanese Patent Office Re. Application No. 2006-552013.
Translation of Notification of Reason for Rejection Dated Feb. 3, 2011 From the Japanese Patent Office Re. Application No. 2006-552009.
Translation of Notification of Reasons for Rejection Dated Jan. 27, 2011 From the Japanese Patent Office Re. Application No. 2007-510233.
Notice of Allowance Dated Oct. 19, 2011 From the Japanese Patent Office Re. Application No. 2006-215045 and Its Translation Into English.
Response Dated Oct. 10, 2011 to Official Action of Aug. 10, 2011 From the US Patent and Trademark Office Re. U.S. Appl. No. 10/597,633.

(56) References Cited

OTHER PUBLICATIONS

Official Action Dated Jun. 14, 2012 From the US Patent and Trademark Office Re.: U.S. Appl. No. 11/660,965.
Official Action Dated Jun. 15, 2012 From the US Patent and Trademark Office Re. U.S. Appl. No. 10/597,602.
Amendment Dated Oct. 28, 2011 in Response to Decision of Rejection Dated Jun. 30, 2011 From the Japanese Patent Office Re. Application No. 2007-510233.
Notice of Allowance Dated Dec. 23, 2011 From the US Patent and Trademark Office Re.: U.S. Appl. No. 11/883,663.
Notice of Appeal Dated Oct. 28, 2011 in Response to Decision of Rejection Dated Jun. 30, 2011 From the Japanese Patent Office Re. Application No. 2007-510233.
Official Action Dated Jan. 11, 2012 From the US Patent and Trademark Office Re. U.S. Appl. No. 10/597,602.
Translation of Notification of Reasons for Rejection Dated Dec. 21, 2011 From the Japanese Patent Office Re. Application No. 2006-552015.
Translation of Official Query Dated Dec. 16, 2011 From the Japanese Patent Office Re. Application No. 2007-529131.
Abe et al. "ICA. A Study of EEG Analysis Method Using ICA", Proceedings of the 1999 IEICE General Conference, p. 149, 1999.
Communication Pursuant to Article 94(3) EPC Dated Feb. 8, 2012 From the European Patent Office Re. Application No. 05703179.1.
Official Action Dated Oct. 1, 2008 From the US Patent Office Re.: U.S. Appl. No. 11/389,773.
Official Action Dated Jul. 22, 2008 From the US Patent Offcie Re.: U.S. Appl. No. 11/389,773.
Supplemental Notice of Allowability Dated Aug. 9, 2011 From the US Patent and Trademark Office Re.: U.S. Appl. No. 10/597,675.
Proceedings Further With the European Patent Applicaiton Pursuant to Rule 70(2) EPC Dated Feb. 23, 2012 From the European Patent Office Re. Application No. 05703181.7.
Supplementary European Search Report Dated Feb. 6, 2012 From the European Patent Office Re. Application No. 05703181.7.
Invitation Pursuant to Rule 62a(1) EPC and Rule 63(1) EPC Dated Mar. 20, 2012 From the European Patent Office Re. Application No. 05703183.3.
Notice of Allowance Dated Apr. 4, 2012 From the US Patent and Trademark Office Re. U.S. Appl. No. 10/597,599.
Translation of Notification of Names of Appeal Examiners and Appeal Clerk Dated Jun. 6, 2012 From the Japanese Patent Office Re. Application No. 2006-552013.
Applicant-Initiated Interview Summary Dated Jun. 11, 2012 From the US Patent and Trademark Office Re. Application No. 10/597,633.
Response Dated Oct. 3, 2011 to Official Action of Sep. 1, 2011 From the US Patent and Trademark Office Re.: U.S. Appl. No. 11/660,965.
Translation of Questioning Dated Jan. 13, 2012 From the Japanese Patent Office Re. Application No. 2006-552013.
Official Action Dated Mar. 19, 2012 From the US Patent and Trademark Office Re. U.S. Appl. No. 10/597,635.
Invitation Pursuant to Rule 62a(1) and Rule 63(1) EPC Dated Mar. 20, 2012 From the European Patent Office Re. Application No. 05703185.8.
Official Action Dated May 14, 2012 From the US Patent and Trademark Office Re. U.S. Appl. No. 10/597,633.
Invitation Pursuant to Rule 62a(1) EPC and Rule 63(1) EPC Dated Mar. 20, 2012 From the European Patent Office Re. Application No. 05703184.1.
Notice of Allowance Dated Jun. 10, 2013 From the US Patent and Trademark Office Re. U.S. Appl. No. 10/597,671.
Official Action Dated Jul. 18, 2013 From the US Patent and Trademark Office Re. U.S. Appl. No. 10/597,633.
Official Action Dated Sep. 26, 2013 From the US Patent and Trademark Office Re. U.S. Appl. No. 10/597,635.
Official Action Dated Jan. 16, 2014 From the US Patent and Trademark Office Re. U.S. Appl. No. 10/597,635.
Communication Pursuant to Article 94(3) EPC Dated Jul. 3, 2012 From the European Patent Office Re. Application No. 05703181.7.
Supplementary Partial European Search Report Dated Jul. 11, 2012 From the European Patent Office Re. Application No. 05703184.1.
Advisory Action Before the Filing of an Appeal Brief Dated Jul. 26, 2012 From the US Patent and Trademark Office Re. U.S. Appl. No. 10/597,633.
Official Action Dated Sep. 7, 2012 From the US Patent and Trademark Office Re. U.S. Appl. No. 10/597,671.
Proceeding Further With the European Patent Application Pursuant to Rule 70(2) EPC Dated Jul. 30, 2012 From the European Patent Office Re. Application No. 05703185.8.
Proceedings Further With the European Patent Application Pursuant to Rule 70(2) EPC Dated Jul. 30, 2012 From the European Patent Office Re. Application No. 05703183.3.
Proceedings Further With the European Patent Application Pursuant to Rule 70(2) EPC Dated Jul. 30, 012 From the European Patent Office Re. Application No. 05703184.1.
Supplementary Partial European Search Report Dated Jul. 11, 2012 From the European Patent Office Re. Application No. 05703183.3.
Supplementary Partiel European Search Report Dated Jul. 11, 2012 From the European Patent Office Re. Application No. 05703185.8.
Applicant-Initiated interview Summary Dated Oct. 25, 2012 From the US Patent and Trademark Office Re. U.S. Appl. No. 10/597,602.
Official Action Dated Sep. 1, 2011 From the US Patent and Trademark Office Re.: U.S. Appl. No. 11/883,663.
Official Action Dated May 9, 2011 From the US Patent and Trademark Office Rc.: U.S. Appl. No. 11/883,663.
Official Action Dated Oct. 17, 2012 From the US Patent and Trademark Office Re. U.S. Appl. No. 10/597,635.
Yoo et al. "Brain-Computer Interface Using FMRI: Spatial Navigation by Thoughts", Clinical Neuroescience and Neuropathology, 15(10): 1591-1595, Jul. 19, 2004.
Communication Under Rule 71(3) EPC Dated Nov. 7, 2012 From the European Patent Office Re. Application No. 05703179.1.
Official Action Dated Nov. 27, 2012 From the US Patent and Trademark Office Re. U.S. Appl. No. 10/597,633.
Applicant-Initiated Interview Summary Dated Feb. 6, 2013 From the US Patent and Trademark Office Re. U.S. Appl. No. 10/597,635.
Communication Pursuant to Article 94(3) EPC Dated Mar. 19, 2013 From the European Patent Office Re. Application No. 05703183.3.
Communication Pursuant to Article 94(3) EPC Dated Mar. 19, 2013 From the European Patent Office Re. Application No. 05703184.1.
Communication Pursuant to Article 94(3) EPC Dated Mar. 19, 2013 From the European Patent Office Re. Application No. 05703185.8.
Official Action Dated Mar. 19, 2014 From the US Patent and Trademark Office Re. U.S. Appl. No. 11/660,965.
Applicant-Initiated Interview Summary Dated Jan. 23, 2013 From the US Patent and Trademark Office Re. U.S. Appl. No. 10/597,671.
Applicant-Initiated Interview Summary Dated Dec. 20, 2013 From the US Patent and Trademark Office Re. U.S. Appl. No. 10/597,633.
Communication Pursuant to Article 94(3) EPC Dated Jul. 17, 2014 From the European Patent Office Re. Application No. 05703181.7.
Communication Pursuant to Article 94(3) EPC Dated May 13, 2014 From the European Patent Office Re. Application No. 06704564.1.
Communication Pursuant to Article 94(3) EPC Dated Jul. 28, 2014 From the European Patent Office Re. Application No. 05703183.3.
Communication Pursuant to Article 94(3) EPC Dated Jul. 28, 2014 From the European Patent Office Re. Application No. 05703184.1.
Communication Pursuant to Article 94(3) EPC Dated Jul. 28, 2014 From the European Patent Office Re. Application No. 05703185.8.
Official Action Dated Aug. 4, 2014 From the US Patent and Trademark Office Re. U.S. Appl. No. 10/597,602.
Kristy et al. "A Robotic Arm 'Smart Exercise System': A Rehabilitation Therapy Modality", Engineering in Medicine and Biology Society, Proceedings of the Annual International Conference of the IEEE Engineering in Images of the Twenty-First Century, XP010088537, p. 1504-1505, 1989.

(56) References Cited

OTHER PUBLICATIONS

Martens et al. "A Friend for Assisting Handicapped People. The Semiautonomous Robotic System 'FRIEND' Consists of an Electric Wheelchair With a Robotic Arm and Utilizes a Speech Interface", IEEE Robotics & Automation Magazine, XP055130671, 8(1): 57-65, Mar. 1, 2001.

Applicant-Initiated Interview Summary Dated Oct. 10, 2014 From the US Patent and Trademark Office Re. U.S. Appl. No. 10/597,602.

Communication Pursuant to Article 94(3) EPC Dated Sep. 29, 2014 From the European Patent Office Re. Application No. 06704564.1.

\* cited by examiner

METHODS AND APPARATUSES FOR REHABILITATION EXERCISE AND TRAINING

RELATED APPLICATIONS

This application is a U.S. National Phase of PCT/IL2005/00136 filed on Feb. 4, 2005. This application also claims the benefit under 119(e) of U.S. Provisional Application No. 60/542,022 filed on Feb. 5, 2004, U.S. Provisional Application No. 60/566,079 filed on Apr. 29, 2004, U.S. Provisional Application No. 60/633,428 filed on Dec. 7, 2004, U.S. Provisional Application No. 60/633,429 filed on Dec. 7, 2004 and U.S. Provisional Application No. 60/633,442 filed on Dec. 7, 2004 the disclosures of which are incorporated herein by reference.

This application is also related to PCT applications, filed by the same applicant as the present application, PCT/IL2005/000138 entitled "Gait Rehabilitation Methods and Apparatuses"; PCT/IL2005/000137 entitled "Rehabilitation with Music"; PCT/IL2005/000135 entitled "Neuromuscular Stimulation"; PCT/IL2005/000139 entitled "Fine Motor Control Rehabilitation"; PCT/IL2005/000142 entitled "Methods and Apparatus for Rehabilitation and Training"; PCT/IL2005/000140 entitled "Methods and Apparatus for Rehabilitation and Training" and PCT/IL2005/000141 entitled "Methods and Apparatus for Rehabilitation and Training", all filed on Feb. 4, 2005. The disclosures of all these applications are incorporated herein by reference.

FIELD OF THE INVENTION

The present invention relates to manipulation of body parts, for example for physical rehabilitation and/or rehabilitation of balance disorders and/or training body parts and/or treatment of pain and/or exercise.

BACKGROUND OF THE INVENTION

After accidents or injuries or strokes, some body functions are damaged and persons often need a rehabilitation process in an attempt to recapture some or all of the damaged body functions.

Rehabilitation may include one or both of two elements: physical rehabilitation and cognitive rehabilitation. Physical rehabilitation attempts to restore physical functioning of damaged body parts, such as muscles. Cognitive rehabilitation attempts to restore cognitive abilities to control the body.

Physical rehabilitation is presently mainly provided by personal attention of a physical therapist that monitors and instructs a patient in performing of certain exercises. Thus, costs for rehabilitation are high and compliance after a patient leaves a treatment center is relatively low.

Some home physical therapy devices are known, for example a product called "backlife", which is described in (wwwdot.backlifedot.com), as on November 2004, provides Continuous Passive Movement ("CPM") of the spine and is also used to relieve back pain.

Accidents or strokes or injuries may cause balance disorders. Balance disorders may occur from damage to the vestibular apparatus (centered in the inner ear), damage to the central nervous system ("CNS"), and/or from postural and strength deficits.

Balance tests, either observational or computerized for detecting and classifying balance disorders have been developed. Balance training exercises are used to treat balance disorders. Known balance-training exercises are "stand from sitting position", "stand on one leg" and "bend forward so you may pick an object from the floor". Balance training can utilize simple tools such as inflatable balance discs, foam rollers, wobble boards, foam pads, mini-trampolines, and other unstable surfaces. An exercise utilizing a wobble board can be for example "while balancing on a wobble board, catch and toss a small light weight ball".

The following three patents relate to balance testing and/or movement coordination: U.S. Pat. Nos. 5,269,318; 5,476,103 and WIPO Publication No. WO 98/46127 entitled "Method and apparatus for the diagnosis and rehabilitation of balance disorders".

Several companies developed balance measurement and/or balance treatment devices. NeuroCom (wwwdot.neurocomdot.com) has several devices for rehabilitation. The Smart Balance-Master from NeuroCom is a posturography training device. It involves a moving platform coupled to a computer monitor. K.A.T. (Kinesthetic Ability Trainer) from www.medfitsystems.com is used for balance testing and/or balance training. Other known devices are BalanceQuest and System 2000 from Micromedical Teclmologies (wwwdot.micromedicaldot.com). System 2000 is a rotational vestibular chair.

U.S. Publication No. 2002/115536 entitled "Balance training device" describes a device that has a seat and performs horse-riding motions.

A rehabilitation system is described in U.S. Pat. No. 6,774,885 assigned to Motels B.V. and is also described in (www-dot.e-motekdot.com). CAREN — a Computer Assisted Rehabilitation Environnlent is described in U.S. Pat. No. 6,774,885. CAREN helps view and analyze balance and coordination disorders.

Patent EP 0 862 930 entitled "An Interactive device with a balance plate" describes a balance plate for training and rehabilitation of equilibrium capacity.

The disclosures of all patents and other publications mentioned in this patent application are incorporated herein by reference.

SUMMARY OF THE INVENTION

An aspect of some embodiments of the invention relates to rehabilitation of a patient while the patient is in a sitting position. In an exemplary embodiment of the invention, a rehabilitation chair system is provided which senses and/or actuates portions of the patient, while sitting down. In an exemplary embodiment of the invention, the chair is selectively unstable. Optionally, the chair is used to rehabilitate balance abilities.

In an exemplary embodiment of the invention, a rehabilitation chair system, comprises a seat adapted for sitting of a human; at least one extender (e.g., extendible and/or articulating element such as a robotic arm) adapted to move relative to said seat; at least one sensor which generates an indication of a balance state of said human; and a controller configured to move the extender while measuring the balance state using the sensor.

In an exemplary embodiment of the invention, rehabilitation includes moving body parts while not losing ones balance. Optionally, the chair system assists a patient in not losing balance.

A particular feature of some embodiments of the invention is that balance training includes targets that provide real kinesthetic feedback. In one example, a target is a moving robotic arm, which once reached can be grasped and leaned on. Forces associated with such movements can be measured as well. Alternatively or additionally, during a balancing or unbalancing activity direct mechanical contact between the moving parts of a patient and a chair may assist in teaching a patient about his kinesthetic sense and/or provide support. Alternatively or additionally, the use of physical motion may be useful for bypassing various cognitive problems associated with strokes.

An aspect of some embodiments of the invention relates to providing a portable rehabilitation system for use in locations such as small clinics, homes, offices, outdoors or places of work.

In an exemplary embodiment of the invention, a rehabilitation chair system is controlled according to a program. Optionally, the program is devised using measurements and tests on a plurality of patients.

In an exemplary embodiment of the invention a plurality of different training programs can be predefined (set). Optionally, programs are tailored to patient parameters. Exemplary parameters are body size and age.

An aspect of some embodiments of the invention relates to treatment and/or rehabilitation of balance disorders. In an exemplary embodiment of the invention, such disorders are treated by rehabilitating using exercises specific to problematic body parts, exercise which coordinate between body parts and/or exercises in which a balancing task of reduced complexity is supported by the chair.

An aspect of some embodiments of the invention relates to rehabilitation of balance in which multiple load areas are measured, for example, at least one load area in addition to feet. In an exemplary embodiment of the invention, load on a leaning arm is measured. Alternatively or additionally, load on a buttock is measured.

An aspect of some embodiments of the invention relates to interactive rehabilitation, in which a complex task is broken into progressive sub-tasks and feedback can be provided during such sub-tasks. In an exemplary embodiment of the invention, a reaching task is provided in which as a person reaches farther, the balancing becomes more complex. Feedback regarding balancing is optionally provided as the reaching progresses.

An aspect of some embodiments of the invention relates to treatment and/or prevention of body aches and pains, such as back pain. In an exemplary embodiment of the invention, a chair system can be used to exercise a back and/or or associated muscle and/or skeleton parts, while is a supported position. Optionally, such exercising is sued for patients after back surgery. Optionally, CPM motion of the spine is supported.

There is thus provided in accordance with an exemplary embodiment of the invention a rehabilitation chair system, comprising:

a seat adapted for sitting of a human thereon;
at least one extender adapted to move relative to said seat;
at least one sensor which generates an indication of a balance state of said human; and
a controller configured to move said extender while measuring said balance state using said sensor.

There is also provided in accordance with an exemplary embodiment of the invention a method for rehabilitation, comprising:

identifying human body parts that need rehabilitation and exercising at least one of said body parts using a chair system which includes moving parts that are adapted to be coupled to body limbs. Optionally, the rehabilitation needed and the exercises are for balance rehabilitation.

There is also provided in accordance with an exemplary embodiment of the invention, a rehabilitation chair system, comprising:

a seat adapted for sitting of a human thereon;
at least one extender adapted to move relative to said seat;
at least one sensor which generates an indication of a balance state of said human; and
a controller configured to move said extender while measuring said balance state using said at least one sensor. Optionally, said extender is mechanically coupled to said seat. Alternatively or additionally, said controller moves said extender responsive to said balance state. Alternatively or additionally, said controller moves said extender and measures a responsive change in balance state. Alternatively or additionally, said seat is adapted to rotate out of plane of the seat.

In an exemplary embodiment of the invention, said seat comprises a back. Optionally, said back is articulated. Alternatively or additionally, said back rotates around a vertical axis thereof.

In an exemplary embodiment of the invention, said seat is adapted to resist said rotating thereof.

In an exemplary embodiment of the invention, said seat is adapted to lift under power at least 10 cm.

In an exemplary embodiment of the invention, the system comprises at least one leg mover adapted to lift at least one leg of the human from a floor on which the leg rests. Optionally, the system comprises at least a second leg mover adapted to lift at least a second leg from said floor. Optionally, said leg movers are adapted to be locked together. Alternatively or additionally, said leg movers are separately movable.

In an exemplary embodiment of the invention, said at least one balance sensor comprises at least one pressure mat for a foot of the human.

In an exemplary embodiment of the invention, said at least one sensor comprises at least one pressure sensor for an armrest of said chair.

In an exemplary embodiment of the invention, said at least one sensor comprises at least one pressure sensor positioned on the seat for a buttock.

In an exemplary embodiment of the invention, said at least one sensor comprises at least one pressure sensor positioned to be placed on a table near said chair.

In an exemplary embodiment of the invention, said at least one sensor comprises at least two pressure sensors symmetrically positioned relative to a person sitting in the chair.

In an exemplary embodiment of the invention, said at least one sensor comprises at least four spatially separated pressure sensors.

In an exemplary embodiment of the invention, said controller drives said extender according to a rehabilitation plan stored within the controller.

In an exemplary embodiment of the invention, said controller drives said seat according to a rehabilitation plan stored within the controller.

There is also provided in accordance with an exemplary embodiment of the invention, a rehabilitation system comprising:

a joint having a common center of rotation for rotation (Phi) and elevation (Theta) angles;
a seat mounted on said joint; and
a controller adapted to perform at least one of: drive said seat and measure a rotation of said seat, according to a rehabilitation plan.

There is also provided in accordance with an exemplary embodiment of the invention, a rehabilitation system comprising:

a chair adapted for sitting of a human thereon;
a leg lift mechanism adapted to lift at least one leg of a human sitting on the chair; and a controller adapted to control the lift mechanism to repeatedly lift the at least one leg of the human, such that a spine of the human is manipulated.

There is also provided in accordance with an exemplary embodiment of the invention, a method of rehabilitation of a person, comprising:

sitting the person in a chair coupled to a robotic assistance device; and performing, with robotic assistance of said device, at least one rehabilitation exercise on said person, said exercise designed to rehabilitate balance, said robotic assistance including at least one of providing motive force by said robotic assistance and providing an obstruction to motion by said robotic assistance. Optionally, said exercise comprises reaching one or more hands. Alternatively or additionally, said exercise comprises lifting and placing an object.

In an exemplary embodiment of the invention, said exercise comprises a manipulation of hands extended away from the body.

In an exemplary embodiment of the invention, said exercise comprises an interactive exercise with feedback as the complexity of the exercise increases.

In an exemplary embodiment of the invention, said performing comprises monitoring a plurality of body parts.

In an exemplary embodiment of the invention, the method comprises monitoring a balance between body sides of the person while performing the exercise.

In an exemplary embodiment of the invention, the method comprises monitoring positions of an organ of the person and analyzing the positions to determine an assistance of the organ to a balance of the person. Optionally, the organ comprises an arm. Alternatively or additionally, the organ comprises a torso. Alternatively or additionally, the organ comprises a leg.

In an exemplary embodiment of the invention, monitoring positions of the organ comprises monitoring movements of the organ.

In an exemplary embodiment of the invention, monitoring positions of the organ comprises monitoring resistance of the organ to motion of another body part.

In an exemplary embodiment of the invention, said robotic assistance comprises moving a body part.

In an exemplary embodiment of the invention, said robotic assistance comprises resisting the motion of a body part.

In an exemplary embodiment of the invention, said robotic assistance comprises preventing loss of balance.

In an exemplary embodiment of the invention, said robotic assistance comprises inducing loss of balance.

In an exemplary embodiment of the invention, said exercise comprises standing up.

In an exemplary embodiment of the invention, said robotic assistance lifts said person.

In an exemplary embodiment of the invention, said exercise comprises torso training.

There is also provided in accordance with an exemplary embodiment of the invention, a method of balance rehabilitation comprises:

performing by a person a task requiring balancing; and monitoring a performance of said task by measuring forces at a plurality of spatially separate load areas on which the person applies force, including at least one load area other than a foot.

BRIEF DESCRIPTION OF THE FIGURES

Non-limiting embodiments of the invention will be described with reference to the following description of exemplary embodiments, in conjunction with the figures. The figures are generally not shown to scale and any sizes are only meant to be exemplary and not necessarily limiting. In the figures, identical structures, elements or parts that appear in more than one figure are preferably labeled with a same or similar number in all the figures in which they appear, in which.

DETAILED DESCRIPTION OF EXEMPLARY EMBODIMENTS

General

The following description includes both rehabilitation apparatuses and rehabilitation methods. Described is a rehabilitation apparatus in an exemplary embodiment of the invention and optional methods to be performed using the apparatus. It should be noted that the usage of a particular apparatus embodiment for certain methods is to illustrate the particular methods, and should not be construed as limiting the apparatus or the method to the particular combination of apparatus embodiment and method embodiment.

Rehabilitation Chair System

Figure 1:
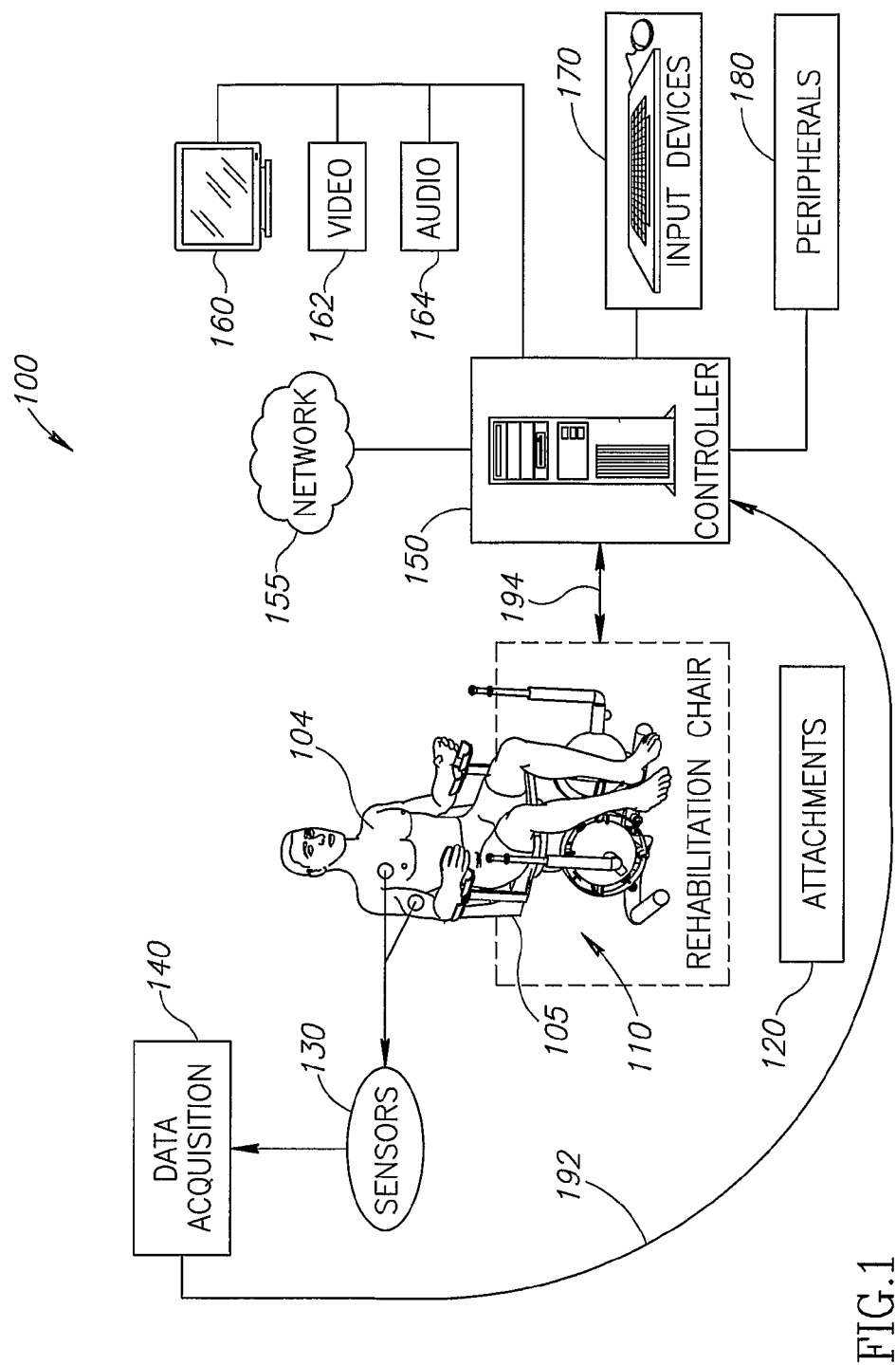
FIG. 1 is a schematic showing of a chair based rehabilitation system, in accordance with an exemplary embodiment of the invention.

In an exemplary embodiment of the invention, the rehabilitation apparatus is a chair, however other rehabilitation apparatuses such as a wobble board or platform are optionally used. FIG. 1 is a schematic showing of a rehabilitation chair system 100, in accordance with an exemplary embodiment of the invention. Person or patient 104 sits on a rehabilitation chair 110. The chair system 100 can be used to train various body parts of the person 104 for rehabilitation purposes and/or treatment of pain. As described herein, the chair system 100 can be used to help recovery and/or training and/or improve movement of body parts such as arms or legs, of the person 104. Optionally sensors 130 are placed on the patient.

System 100 acquires data and transfers it to controller 150. Data such as positions and orientations of chair movable parts and/or person's body parts may be acquired by chair 110 and transferred by the chair to the controller. Data may be acquired, by data acquisition unit 140, from sensors 130 attached to the person, and transferred to controller 150.

The controller runs various programs and processes data transferred to it. The controller then provides feedback, such as physical updating of the chair by moving chair parts to certain positions. The controller can also provide other types of feedback, for instance updating a display 160. Additional information about controller 150 is described in section "controller" below.

Rehabilitation Using a Chair System

Figure 2:
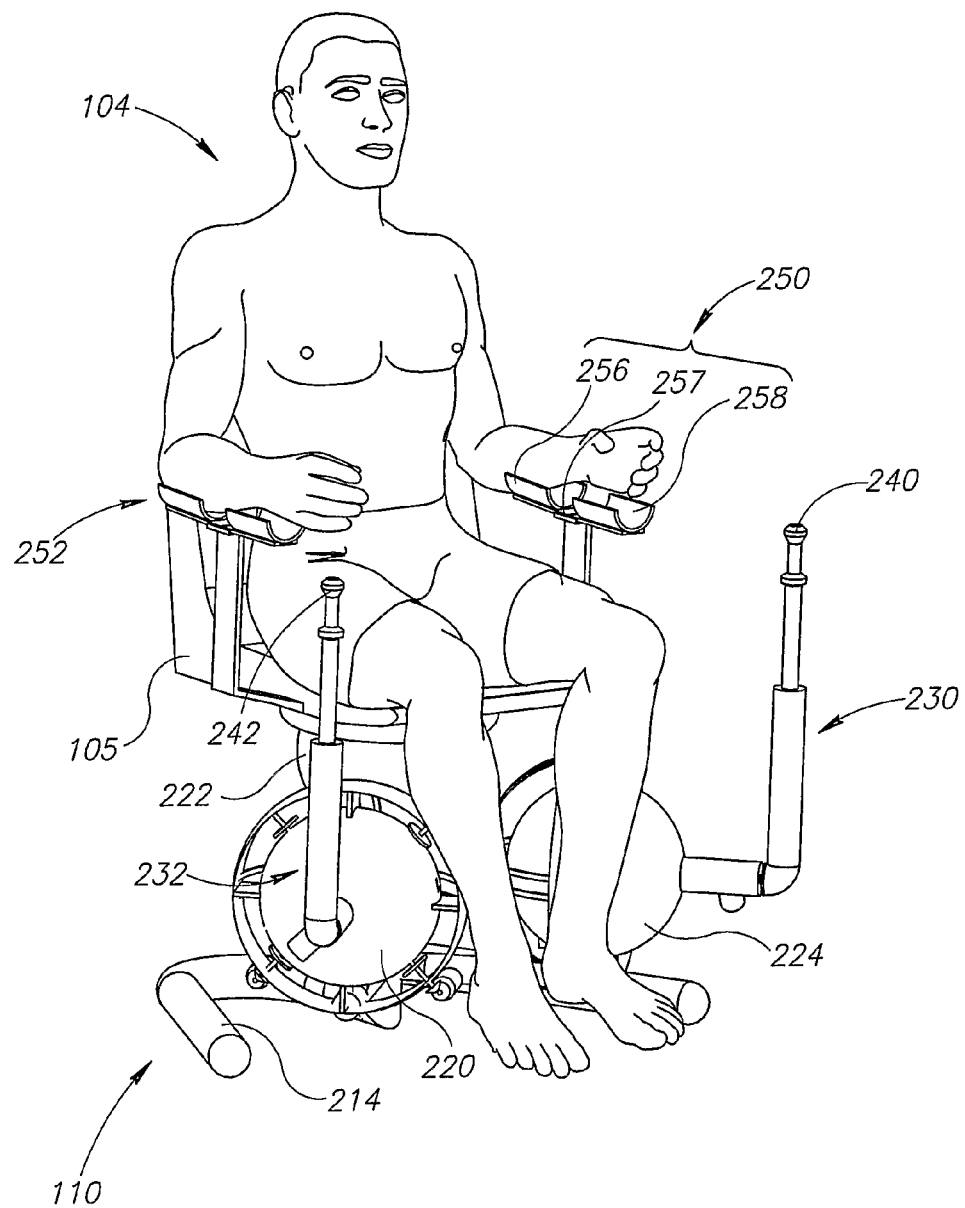
FIG. 2 is a schematic showing a rehabilitation chair, in accordance with an exemplary embodiment of the invention.

FIG. 2 illustrates a rehabilitation chair 110, in accordance with an exemplary embodiment of the invention. Parts comprising this chair are described below, for instance, when describing methods that make use of the chair.

Figure 3:
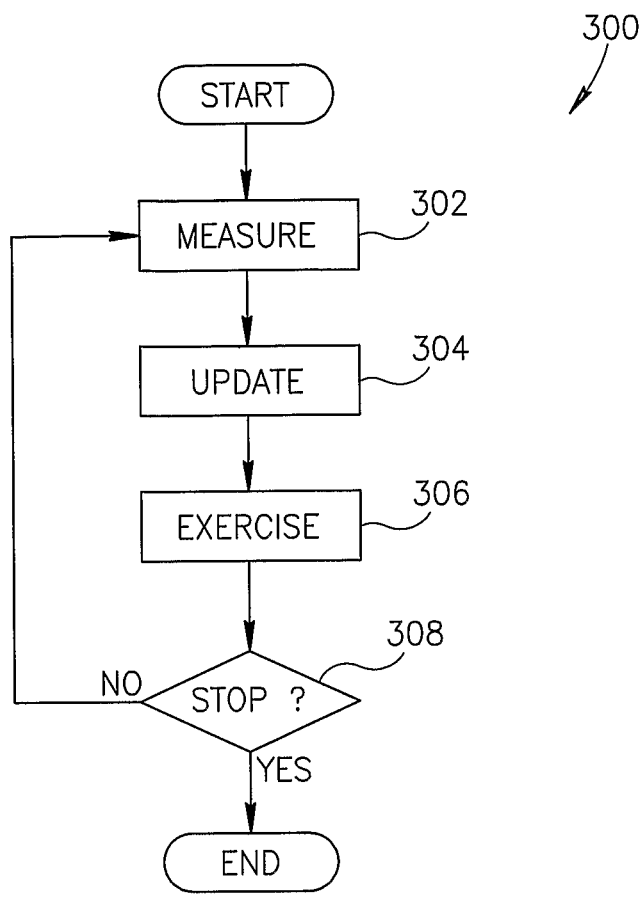
FIG. 3 is a flowchart of a method of using a rehabilitation chair, in accordance with an exemplary embodiment of the invention.

Flowchart 300 of FIG. 3 together with FIG. 1 describes a method of rehabilitation in an exemplary embodiment of the invention. Later below a plurality of chair designs are described and various rehabilitation methods that can be performed with those chairs are described. For example, a rehabilitation method described below is physically assisting a patient to move the patient arms and in this way train the patient arms.

At act 302, various measurements of patient 104 parameters and/or of chair 110 parameters are performed. The measurements involve using various sensors. Sensors may be part of the chair 110 and indicate, for example an off-balance position of the chair. Optionally sensors, such as 130, are attached to the person 104 and indicate, for example, a body position and/or exerted force.

In an exemplary embodiment of the invention, a balance state of a person may be extracted from the indications, indicating the type and/or quality of balance of the person. In one example, an "off-balance" situation is identified when chair 110 is supporting the person unevenly. In another example, a balance state indicates the balance between forces applied on either part of the body. In another example, the balance state includes an indication of the role of various supports (such as chair back and leg supports) in maintaining the balance. In another example, the balance state includes an indication of the relative center of gravity and the support (e.g., chair seat) to indicate stability. In another example, the balance state indicates the stability based on type, amplitude, organization and/or existence of rhythmic motion of the person, for example in shifting loads between different support positions.

At act 304 the measurements are used to update various elements of system 100, such as, a training program for the patient and/or moving chair parts to certain positions. Moving chair parts can assist the person in carrying out tasks and/or provide biofeedback to the person. In an exemplary embodiment of the invention, the moving chair parts are used to set up a target for the patient to reach or to prevent his falling out.

At act 306 patient's body parts are exercised (trained) individually or together. Usually training is according to a program. Optionally a program runs on controller 150. A program may be prepared in advance, and may be devised by conducting preliminary tests. In one example, the program is (in a very simplified form): "first train in sitting straight without support and then train with an unbalanced chair". More details are described below.

At act 308 it is determined if the patient should continue exercise. Rehabilitation sessions may continue a significant period of time, for example, daily or twice weekly for several weeks or months. Over this time period, the type, complexity and/or difficulty of exercises performed may change.

Figure 4:
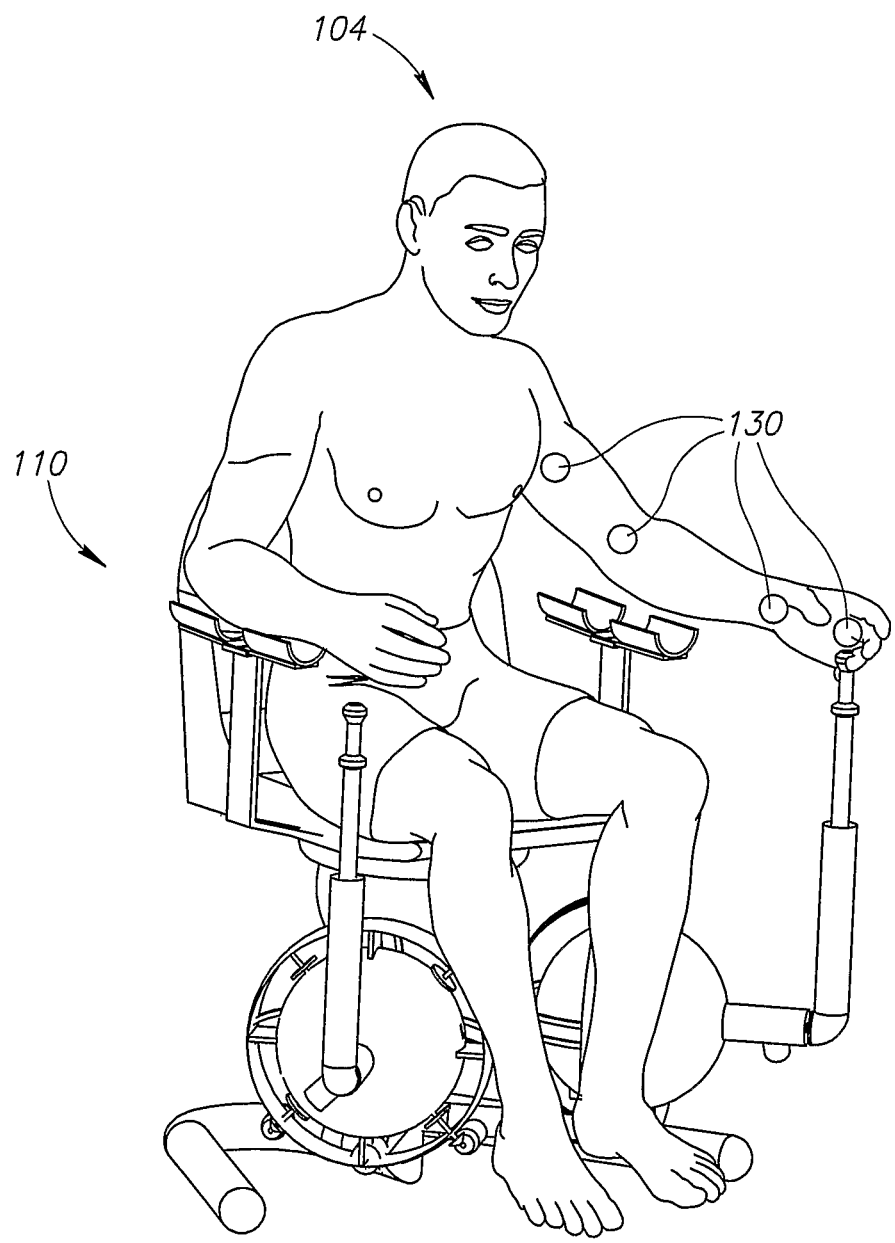
FIG. 4 is an illustration of a person being trained with a rehabilitation chair, in accordance with an exemplary embodiment of the invention.

FIG. 4 illustrates training one arm of person 104 using chair 110. Later below, training methods and motions, such as motions of arms and motions of legs, are described.

"Go with" Method

Figure 5:
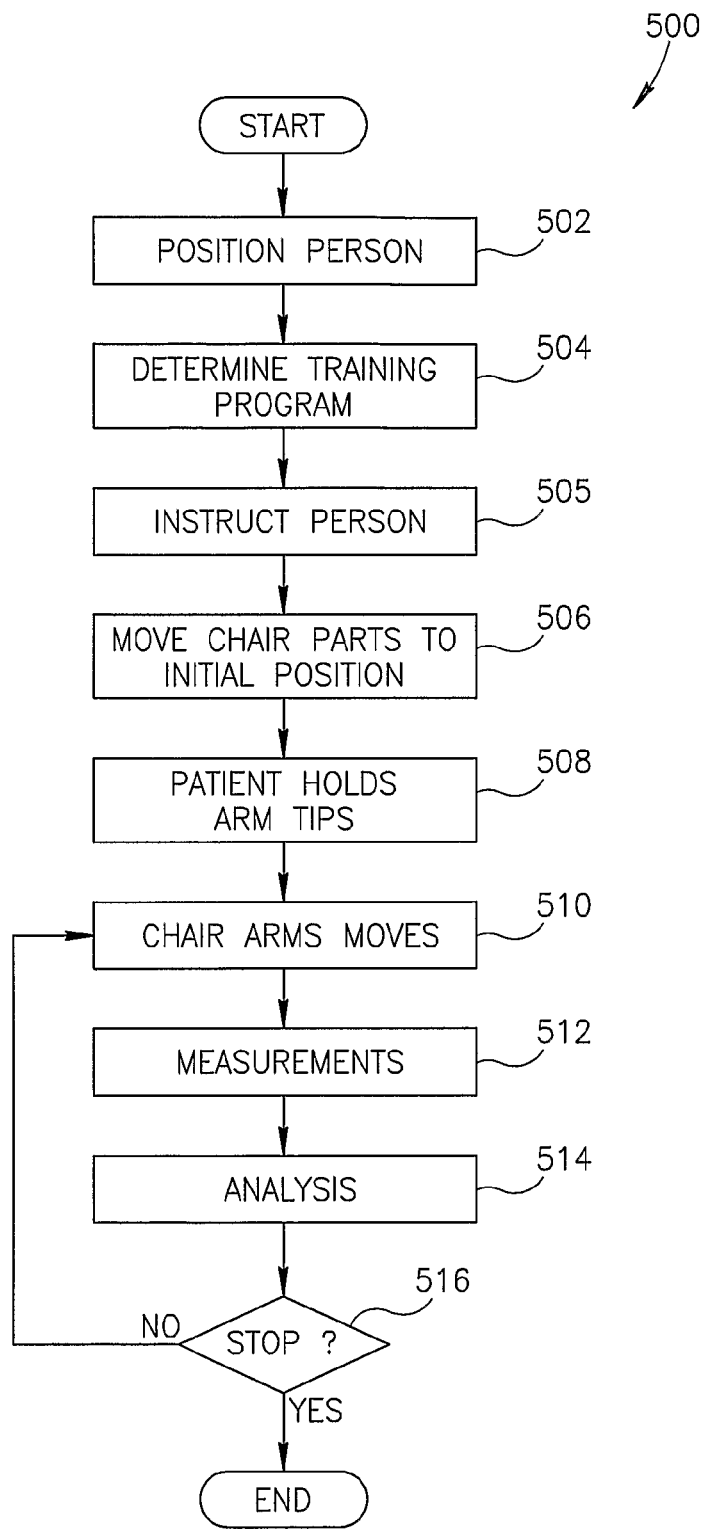
FIG. 5 is a flowchart of a method of using a rehabilitation chair, in accordance with an exemplary embodiment of the invention.

Flowchart 500 in FIG. 5 describes a method ("go with" method) that can be used for balance training and for rehabilitation of a patient's back. This method is illustrated with the chair of FIG. 2. At act 502, patient 104 is positioned on chair 110. The patient sits on seat 105 and his arms are placed on armrests 250 and 252. Armrest 250 in FIG. 2 is optionally comprised of various harnesses 256 and 258, and a harness support 257 which are optionally used depending on each individual patient's need. Arm rest can optionally be floating (e.g. by using air spring) so it can at least partially support the patient's hand. The patient is required to move with the movement of the chair arms while maintaining his balance. The chair may be stable or unstable and various levels of support may be provided (e.g., high or low chair back, chair arms, foot rest, straps (for torso, arms and/or legs) and/or a harness).

At act 504 a training program, for instance to carry out a "go with" method, is determined.

At act 505 the person is instructed what to do. Instruction can be audio and/or video, possibly using a computer generated video generated on the fly by system 100 according to the action to be performed. Optionally, instructions are conveyed to the patient using a virtual reality presentation. In an exemplary embodiment of the invention, system 100 is used to give a demonstration, while a user is holding on or not.

At act 506 chair arms 230 and 232 move towards the hands of the patient at a position that the patient can grab or hold the chair arms. A patient 104 holds a chair arm at a chair arm tip (act 508). Chair arm tip 240 is attached to chair arm 230 and chair arm tip 242 is attached to arm 232. Optionally, various handles, restraints, sensors and/or moving elements are attached to the chair arms 230 and/or 232. In an exemplary embodiment of the invention, an element which gives a sensation of a force field is provided. In another example, a separate element for moving a wrist is provided. In some embodiments of the invention, a sensation attachment is included that provides the patient with varying touch-related sensations, such as tickling. Optionally, the patient uses a sensation attachment for therapy involving surface textures, for example identifying roughness and/or smoothness.

In an exemplary embodiment of the invention, each chair arm is connected to a ball based mechanism that allows movements of the chair arm, see FIG. 2. In particular chair arm 230 is connected to ball based mechanism 224 and chair arm 232 is connected to ball based mechanism 220. In an exemplary embodiment of the invention, the ball mechanism includes a brake for applying varying force. Optionally the brake is a ring that applies selectable force to the ball as the ring is brought closer to the ball's center. Optionally, the ball is moved using one or more motors, for example stepper and/or servo motors. A handle on the ball is optionally moved using a linear actuator. Encoders for determining chair arm position and/or force sensors for determining chair arm forces are optionally provided. Alternatively, robotic articulated arms may be used.

The chair arms are provided with movement in the x, y and z axes through the ball mechanisms 220 and 224. For example, the patient 104 can use the chair arms 230, 232 to simulate a rowing motion. Optionally, the chair arms 230, 232 can be used to simulate a cross country skiing motion. The chair arms can be moved opposite of each other, for example in a walking motion (right arm forward, left arm back). It should be noted that the chair arms 230, 232 optionally operate and move independently of each other. Optionally a chair arm is an articulated arm, which supports movement in 3D space. In an exemplary embodiment of the invention, at least one chair arm is provided with up to six degrees of freedom. Optionally at least one chair arm is telescoping, adjusting the heights of the arm tips 240 and 242. Alternatively, the chair arms may be set up to act in mirror of each other, for example, a master-slave relationship in which one chair arm causes movement of the other chair arm. In an exemplary embodiment of the invention, the master-slave relationship is implemented through the controller or through a mechanical linkage.

In the "go with" method, at act 510 at least one chair arm 230 and/or 232 moves in relation to the patient 104. As the chair arm moves, the patient is instructed to try to maintain a hand hold on the chair arm tip. The arm can move in any direction relative to the patient, away from or towards, up or down, left or right, or any of these directions in combination. Chair arm motion can be fast or slow, the speed of motion is variable. In an exemplary embodiment of the invention, the chair 110 also moves, as described in below, and is utilized to provide additional varieties of motion in relation to the chair arms 230 and/or 232. In some cases, the patient is instructed to apply and/or maintain a certain force level and/or a varying force level. Such force levels may be indicated by the response of the chair arm, which may allow motion in one trajectory, optionally with resistance, but not allow motion in other directions.

As the patient moves to "go with" the moving arm, sensors 130 optionally attached to both the patient and the chair register the movements of the patient relative to the chair and chair arms at act 512. In an exemplary embodiment of the invention, sensors determine the position of chair parts such as chair arm 230 and/or arm 232 and/or tip 240 and/or tip 242.

At act 514, analysis is carried out by system 100. The analysis can be used to modify the training program and/or to move various chair parts and/or provide other feedback to the person 104. In an exemplary embodiment of the invention, controller 150 analyzes balance and coordination movement patterns as they happen. This enables the chair system 100 to immediately intervene and influence and/or correct the patient's movements. For example, sensors 130 can detect if the patient 104 is leaning too far or is exerting an inordinate amount of pressure on a chair arm such that if allowed to continue, the patient would fall out of the chair or possibly sustain further injury. In an instance such as described, the chair could compensate by tilting backwards to force the patient to settle backwards into the chair, thereby avoiding a patient fall. In addition to providing correcting chair movements based on sensor readings, the patient and a supervising health care professional can examine and analyze the sensor readings in order to measure patient progress and determine further rehabilitation strategy. It should be noted that corrective movements can also be instigated by the chair arms 230 and/or 232. At act 516 it is determined if the patient should continue exercise.

In an exemplary embodiment of the invention, controller 150 controls chair 110, according to a program. The controller controls for instance movable parts such as chair arms 230 and/or 232. The controller executes a rehabilitation method, such as the method of flowchart 500.

Motions of a Seat

Figure 6:
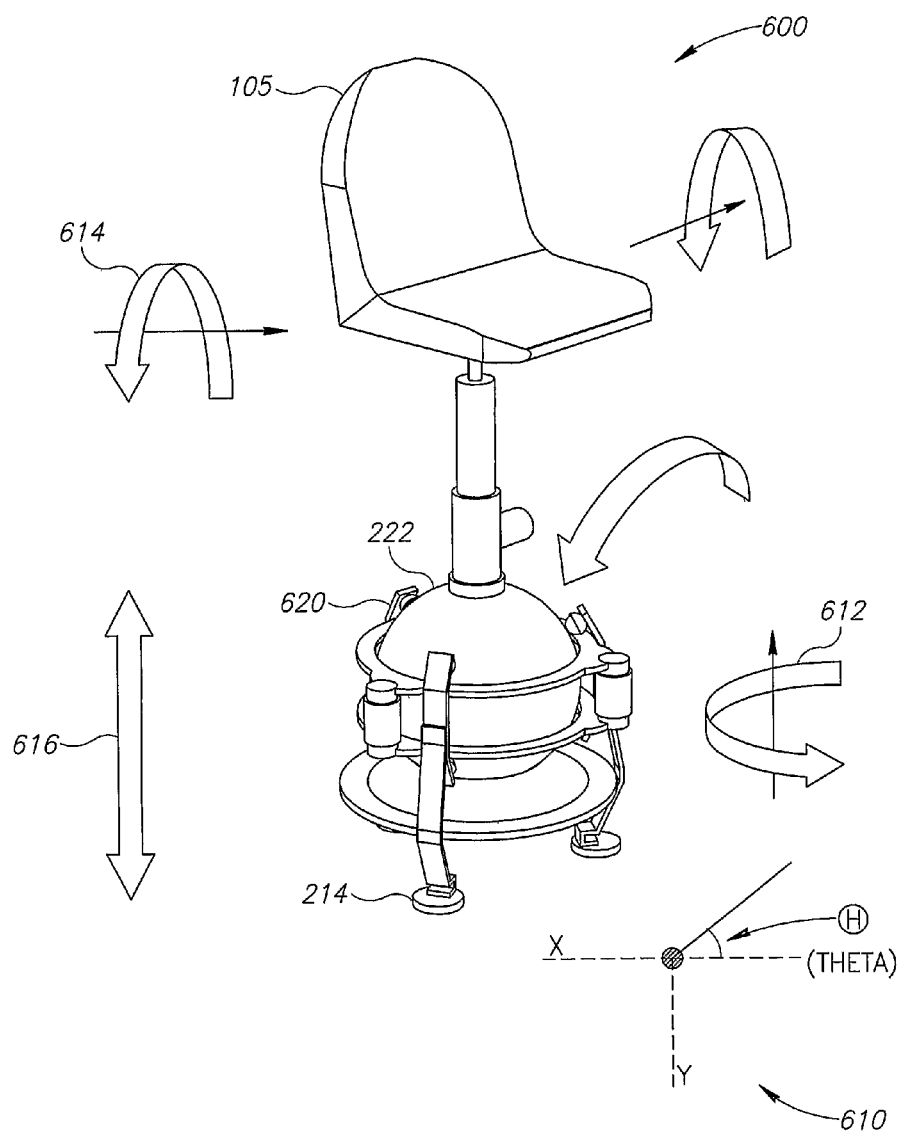
FIG. 6 is a schematic showing of a basic chair based rehabilitation device, in accordance with an exemplary embodiment of the invention.

FIG. 6 is a schematic showing of a basic chair 600, which is a version of chair 110, in accordance with an exemplary embodiment of the invention. Both chairs 110 and 600 comprise a seat 105; a base 214; an optional ball-based mechanism, or other rotary ball bearing arrangement (e.g. a dual gimbal) 222 that connects to the seat and controls seat movements. FIG. 6 shows also a brake mechanism (620). Brake mechanisms can be used to control the movement of the chair along particular axes. For example, if movement along the x axis is undesirable, a brake can be applied to the surface of the ball mechanism 222 to prevent movement of the chair in that direction. Brakes are generally less expensive than motors and require less power. FIG. 6 demonstrates some possible movements of seat 105. Three types of movements of the seat, in X-Y direction (612), in X-Z direction (614), and in Z direction (616) are shown; however movement combining all three axes is possible. In addition, translation motions along the X-Y plane can be provided, for example using suitable linear actuators.

In an exemplary embodiment of the invention the controller 150 may transmit X axis, Y axis, and Z axis positions and rotations to chair 600. For example, if a person 104 leans forward, the chair 110 would respond and adjust the seat 105 according to a training program.

In an exemplary embodiment of the invention, the seat and/or the seat back can rotate around the seat vertical axis. Optionally, this rotation is used to assist or resist torso rotation by a patient. Optionally, the seat back is divided into parts, so, for example, the shoulder section of the seat back can rotate while the lumber section of the seat back remains static.

In an exemplary embodiment of the invention, the seat 105 is moved by the controller 150 while the patient 104 remains substantially stationary. This is desirable when the posture of the patient 104 is measured, for instance.

In an exemplary embodiment of the invention, the patient is exercised by moving the chair 110 or chair arms 230 and/or 232 such that the patient must move with the chair and/or chair arms while trying to maintain balance. The pressure exerted by the patient on various chair parts, including the chair arms, is measured and analyzed. Optionally, this is achieved by having the patient hold the chair arm tips 240, 242 as they move and then using sensors attached to various system parts such as the chair arms, chair arm tips, and/or a foot rest (or floor mat) to gauge the force applied by the patient.

In an exemplary embodiment of the invention, the chair is allowed to rotate and pivot freely, or at a reduced rate (e.g., using the brake), wherein the patient must balance the chair without assistance from the controller 150. As the patient corrects to maintain balance in the chair, the patient's movements can be measured and analyzed in order to measure rehabilitation progress and to formulate further rehabilitation strategy. Optionally, the patient balances the chair while also using chair arms 230 and/or 232. In particular, what might be measured is unbalanced application of forces, differences in time in application of forces (between sides) and the activity of back and stomach muscles (e.g., as measured by EMG).

Figure 10:
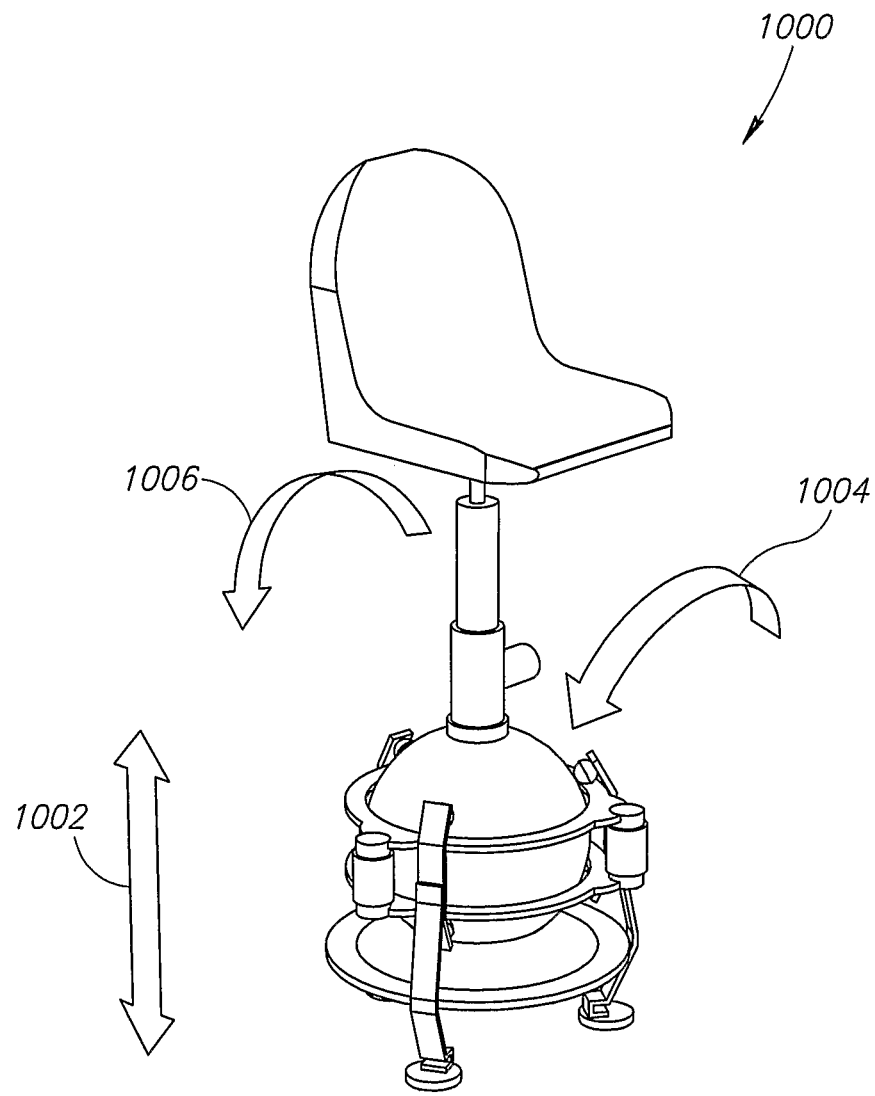
FIG. 10 is an illustration of a rehabilitation chair showing various ranges of movement in an exemplary embodiment of the invention.

FIG. 10 depicts three basic axes of motion 1002, 1004, and 1006 that are possible with an exercise chair 1000, in an exemplary embodiment of the invention. 1002 is motion of the chair 1000 in a z-axis. Arrows 1004 and 1006 symbolize exemplary rotational motions which can be achieved as a result of mounting the chair on a gimbal.

Figure 13:
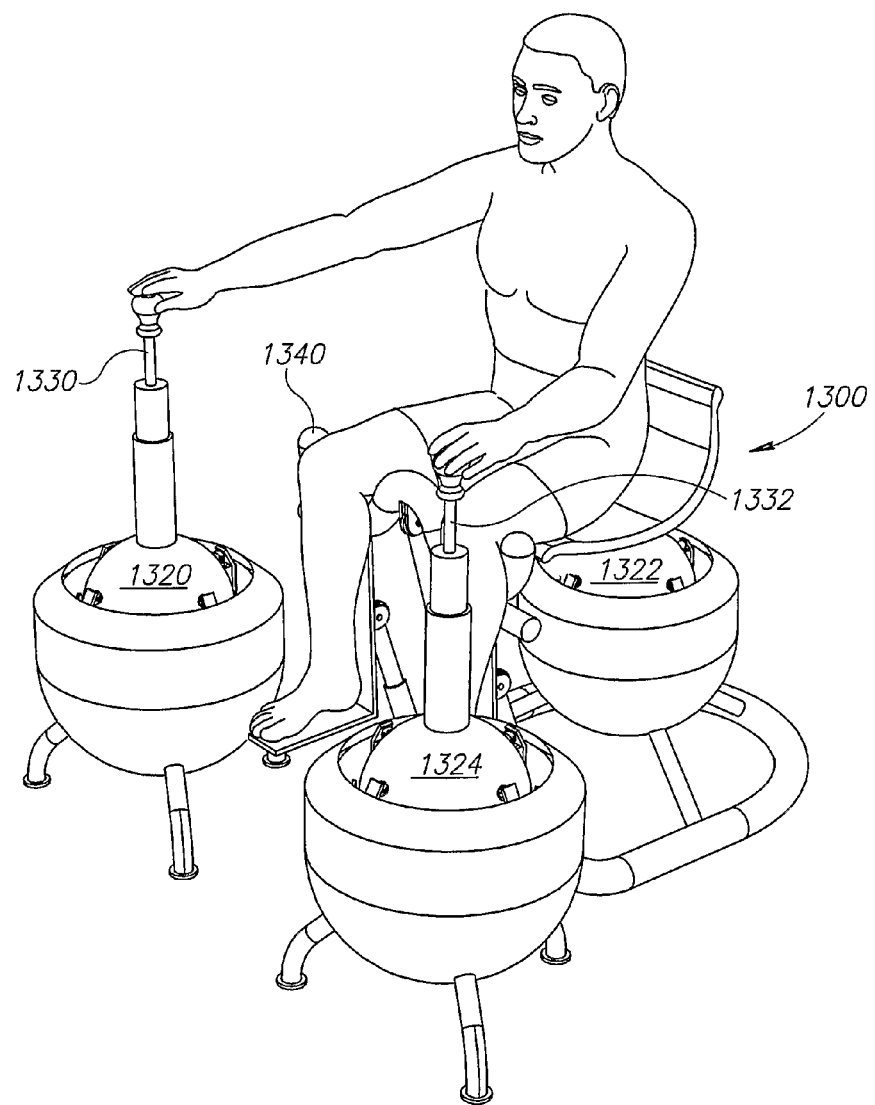
FIG. 13 illustrates a version of rehabilitation chair, in accordance with an exemplary embodiment of the invention.

FIG. 13 depicts an exemplary embodiment of a rehabilitation chair 1300 with chair arms 1330, 1332 that are separate from the chair 1300. The chair arms 1330, 1332 are shown connected to ball mechanisms 1320, 1324 similar to the ball mechanism 1322 of the chair itself. Optionally, this chair is provided with knee supports 1340 which provide CPM to the patient for the strengthening of the back. CPM is used for the treatment of back pain and is discussed in more detail in below. This chair 1300 is optionally used with the attachments and in the manner described for chairs 110 and 600.

Alternatively, chair 1300 may be used to move a patient into a position where he is supported only by his buttocks and while he may be required to move arm(s) and/or leg(s) according to a certain protocol. Optionally supports for the arms and the legs are provided and are used to measure applied forces. Optionally, chair 1300 has a back which flattens out so that the patient can exercise lying down, while having started from a standing or sitting position.

"Reach Forward" Method

Figure 7:
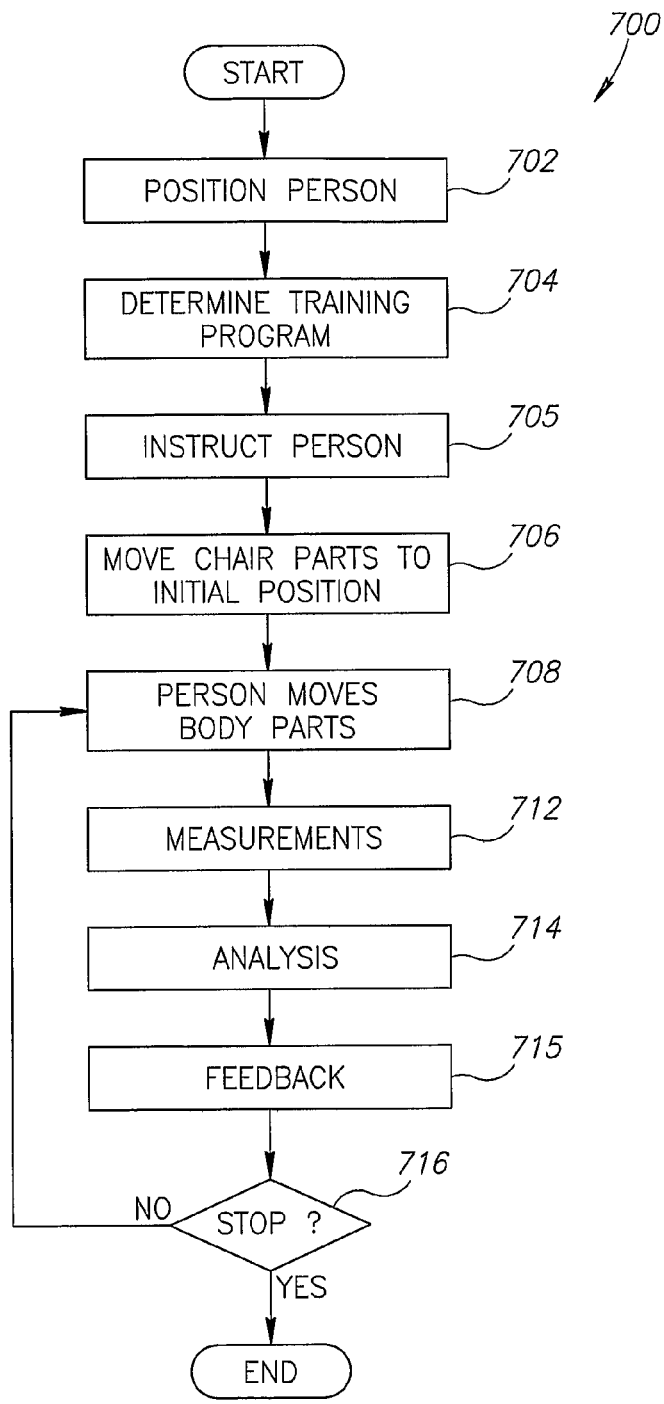
FIG. 7 is a flowchart of a method of using a rehabilitation chair, in accordance with an exemplary embodiment of the invention.

Flowchart 700 in FIG. 7 describes a method ("Reach forward" method) that can be used for balance training. It is noted that "reach forward" is merely a name for the method and in fact, the patient reaching can be performed in any direction (e.g. up, sideways, etc.). This method is illustrated with the chair of FIG. 2. At act 702, patient 104 is positioned on chair 110. At act 704 a training program is determined. In this case a program to carry out a "reach forward" method. At act 706, the chair parts are moved into an initial position for exercise. For example, where a patient is reaching for a target, chair arms may not be necessary or desirable and hence may be removed.

The patient is instructed to move a hand to a start position and then to reach forward as far and as fast a possible (act 705). The chair provides assistance or resistance (act 715) depending on measurements (act 712) it performs. For example, the chair system measures (act 712) the person's body parts positions and orientations and in response to these measurements the chair system applies forces through the chair system to the person (act 715). Optionally, the chair ability to move is limited to specific desired ranges of motion. For example, only back/front motion is allowed without sideways motion.

Graphical and/or audio and/or video feedback can be given to the person during reaching (act 715). At act 714, analysis is carried out by system 100. The analysis can be used to modify the training program and/or to move various chair parts and/or provide other feedback to the person 104. A therapy program may consist for example of a number, N, of targets and a number, M, of reaches the person is supposed to do for each target. For example, targets are arranged over a broad range of motion (e.g. from straight up to straight forward to sideways). Optionally, targets are clustered close together. Targets are presented based on the patient's needs for rehabilitation. In addition to varying target location, in an exemplary embodiment of the invention the patient is instructed to reach for the targets with variable speed and/or force. In order to focus rehabilitation on a particular part of the patient's body, parts of the patient may be constrained, or the patient may be instructed to hold them still, to prevent "cheating" or unwanted assistance from healthy body parts. Sensors are optionally used to monitor "cheating". In an exemplary embodiment of the invention, rehabilitation includes resistance training (e.g. use of weights).

Patient 104 is instructed (act 705) to begin movement (act 708) with the hand resting on the armrest and moving slowly towards a target. Targets may be positioned on a substantially vertical board optionally attached to the chair, and at a distance the person can reach and in front of the person. Sensors may be located on the hand. In an exemplary embodiment of the invention, the board includes lights (which indicate target locations) and sensors for measuring force. Optionally, the board includes position sensors and/or an actuator to move it to known positions. Optionally, the board includes a track which a target can travel on, for example if a sensor is provided on the target itself and not on the whole board. The patient moves towards a target until the patient can no longer move towards it or until the target has been reached. In an exemplary embodiment of the invention, the person gets feedback (act 715) on how close his hand was to the target (for example using a proximity sensor or a position sensor on the hand), about the velocity of moving the arm, and about the smoothness of the movement. In an exemplary embodiment of the invention, the target is a robotic arm tip which includes, for example force sensors and/or position sensors. At act 716 it is determined if the patient should continue exercise.

In an example of a writing task, a pen having a position and a contact/pressure sensor is used, for example, as known in the art of writing detecting whiteboards.

Figure 8:
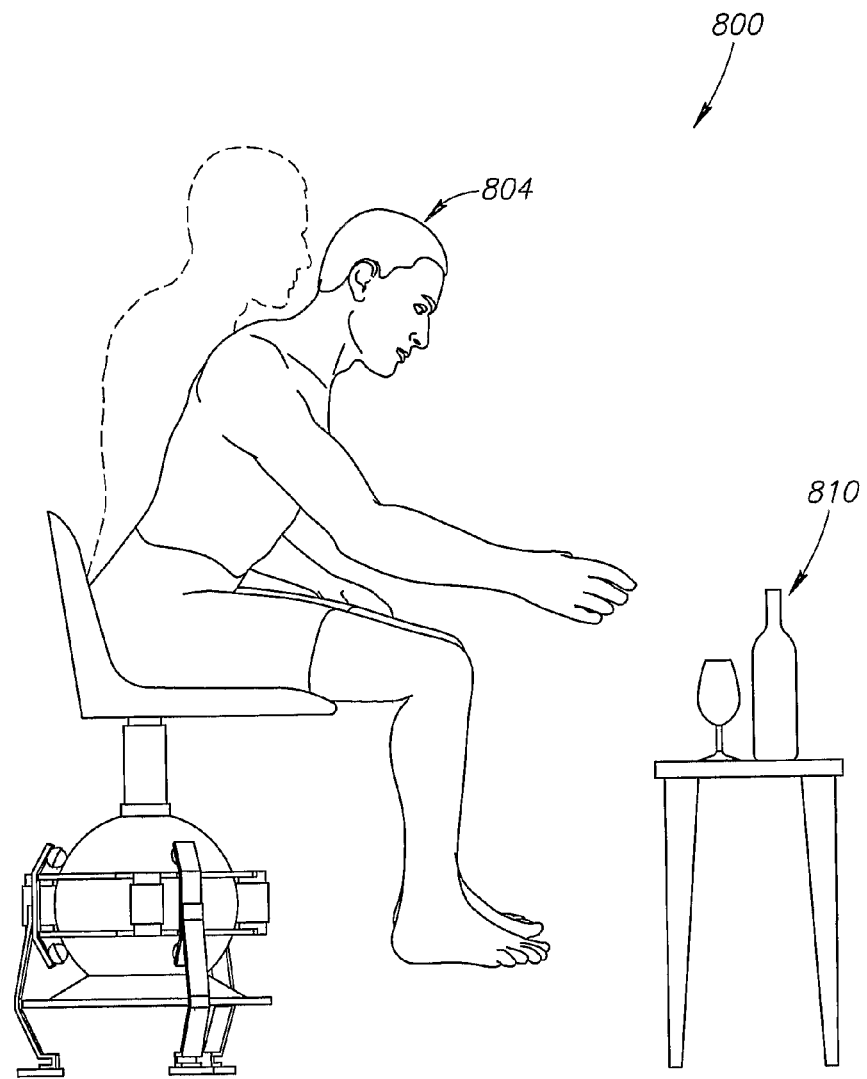
FIG. 8 is an illustration of a person being trained with a rehabilitation chair, in accordance with an exemplary embodiment of the invention.

Turning now to FIG. 8, an illustration of a person reaching forward using a rehabilitation chair 800 is shown in accordance with an exemplary embodiment of the invention. In this case, the target, N, is a bottle 810. In an exemplary exercise, the patient 804 is initially instructed to reach slowly towards the bottle 810. After successfully reaching slowly towards the bottle, the patient is then instructed to reach incrementally faster, and optionally farther, towards the bottle. Optionally, the chair 800 assists the patient with the reaching towards the bottle, by rotating forward slightly. Optionally, an articulated back rest is used to "push" the patient closer towards the bottle. In an exemplary embodiment of the invention, sensors are used to monitor the status of the patient and the chair as the patient 804 reaches towards the bottle 810. Analysis of the sensor measurements is used to detect deficiencies in the patient's balance and strength. These deficiencies are then rehabilitated specifically, optionally using the apparatuses and methods described herein.

In an exemplary embodiment of the invention, the patient is also encouraged to refine motor control by conducting exercises such as pouring, or simulating pouring, from the bottle, while maintaining his balance An Exemplary "Correct Balance" Method In an exemplary embodiment of the invention, a patient is taught how to achieve correct balance using the measurements of force exerted by a plurality of body parts and, optionally, biofeedback. Optionally, a patient is rehabilitated to achieve a balanced condition using different combinations of one or more limbs. For example, the patient can receive balance rehabilitation for balancing on only one foot, but not both at the same time. As described herein, a patient's motion and/or balance can be measured utilizing a plurality of sensors positioned on and around the patient and on and around exercise apparatuses. Optionally, a vector summation of all the measured forces can be calculated to determine if a patient is correctly balanced. What is considered correct balance can be determined by a fabricated goal balance profile, by comparison to the patient's healthy profile, by comparison to another person's healthy profile and/or by any other reasonable method of establishing a standard of balance for the patient. Optionally, a patient's balance profile is tracked over the course of time in order to measure progress and to assist with rehabilitation planning.

In an exemplary embodiment of the invention, the measurements made by the sensors described herein are used to determine if the patient is exerting too much force in a particular area, or not enough force. For example, if the patient is relying too much on the left leg and not enough on the right leg and is therefore, not perfectly balanced, the sensors will measure the imbalance and the system will attempt to assist the patient into a balanced condition. Optionally, when the system 100 determines the patient is in an off-balance condition, it provides feedback to the patient in order to prompt the patient to respond in a manner that will help to correct the off-balance condition. Feedback is optionally provided to the patient in an audio format and/or on a video display. In some embodiments of the invention, feedback is delivered in the form of vibration or other tactile stimulus. Optionally, feedback is directed to a specific area of the body which is not being used appropriately for achieving a balanced condition.

Additional Chair Details

As described above, various sensors can be affixed to the patient and/or the various chair components in order to accurately gauge the progress of the patient's rehabilitation in exemplary embodiments of the invention. A wide variety of sensors can be used either alone, or in combination, for this purpose. The sensors can be loosely divided into two types: the first are sensors pertaining to the patient (e.g. body part location, physiological responses), while other sensors are used to gauge the disposition of the chair (e.g. position/orientation of chair components).

In order to gather information on the patient during rehabilitation, sensors are optionally attached to the patient's body. For example, positional sensors are optionally attached to body parts such as the arms, chest, head, feet, hands, and/or legs. These positional sensors are used to determine the location of the various body parts while exercising. Analysis of these location measurements assists with recognizing overall patient movement, including overcompensation for weak body parts by stronger body parts and the like. Used in conjunction with the "reach forward" method of rehabilitation, for example, positional sensors can estimate the accuracy and precision of the patient's reach.

Another type of sensor that is optionally used during a patient's rehabilitation is a pressure sensitive sensor. Through the measurement of a patient's exerted pressure in a particular location (e.g. chair arm tip 242), it can be determined how dependent the patient is on that body part for stability and/or body control. Pressure sensors are optionally used with the hands, legs, feet, arms, rear end, head, and torso. In an exemplary embodiment of the invention, analysis of the collected pressure data illustrates if the patient is balanced, and if not, where the deficiencies in balance are situated. For example, pressure sensors used in conjunction with the "going with" method can determine if the patient's balance is deficient if during chair movement the patient exerts an inordinate amount of pressure on a particular chair arm tip. This inordinate amount of pressure would tend to indicate that the patient can't adequately balance when moving in that direction and as a result relied on the chair arm tip to maintain balance. The patient's rehabilitation program could then be tailored to work on balance moving in that direction to overcome the deficiency. Force can optionally be measured using pressure sensors. Used in conjunction with the "reaching forward" method, a patient who extends towards a target can activate a pressure sensor which detects how much pressure (i.e. force) the patient could exert on the target. In an exemplary embodiment of the invention, pressure sensors are used for measuring both strength and balance in combination.

In an exemplary embodiment of the invention, other sensors, such as muscle tension and electromyography ("EMG") sensors are used to monitor a patient's physiological responses to rehabilitation. Analysis of measurements taken from these sensors help identify which parts of the patient require further rehabilitation and allow planning of future rehabilitation strategy. Optionally, pulse measurement or breathing rate sensors are used.

In addition to or alternatively to sensors for monitoring the patient, sensors are optionally provided for monitoring the operation of a rehabilitation chair in an exemplary embodiment of the invention. Sensors are optionally affixed to any component of the rehabilitation chair for tracking for example the position of, power and/or force applied to those components. One type of sensor of this purpose is a magnetic-based position tracking sensor. Ultrasonic and optical position sensors are known as well. Of particular use is comparing sensor readings from the chair with sensor readings from the patient. Comparative analysis of this data indicates patient response to specific movements from the chair. Deficiencies in the patient in response to these chair movements point to areas needing further rehabilitation.

In an exemplary embodiment of the invention, motive force for the chair is provided by at least one motor in operational communication with the ball mechanism 222. Optionally, at least one brake is provided to prevent movement of the ball mechanism 222 in a particular direction, or at all. Furthermore, a motor is optionally provided to assist with chair motion along the z-axis. In an exemplary embodiment of the invention, a position encoder is used with a motor in order to determine the amount of movement imparted to the ball mechanism 222.

Speed and directional movement of the chair is variable, in an exemplary embodiment of the invention. As shown in FIG. 6, the chair optionally moves in the x, y and z axes. The speed of the motor is adjustable to provide movement to the chair ranging from stop to relatively fast. In addition to active control of the chair rotational speed, the chair can be completely unfettered, or provided with only intermittent motor movement Optionally, the chair moves to provide supplemental support for patient movement. In an exemplary embodiment of the invention, the chair responds slowly to gravity, for example including friction (e.g., a brake or using the motor), which simulate lower gravity. Optionally, responses to a user's motion can be at normal or higher than normal speed. Optionally, a safety restriction on miss-balancing (e.g., rotational movements) of the chair is also provided. Alternatively or additionally, there is a threshold below which the chair does not misbalance.

Chair Usage

It should be noted that the rehabilitation devices described herein may be used at home, at care centers, such as old age homes, at hospitals and at rehabilitation centers. In an exemplary embodiment of the invention training can be done by using games and/or competitions and/or tournaments. Optionally, multiple chair systems are interconnected by a network, for example a LAN or an Internet 155 on FIG. 1.

In an exemplary embodiment of the invention rehabilitation can be with or without assistance. For example, once a patient sits down, he can exercise without assistance. Some patients will require assistance and/or strapping-in. Optionally, monitoring and/or management of a rehabilitation session is effected remotely, for example over telephone lines or over an Internet, possibly form a central location.

In an exemplary embodiment of the invention, a chair is used for testing a patient's abilities. Optionally such a chair is used for follow-up of a patient that completed rehabilitation.

Optionally, during rehabilitation, a record is kept of progress of a patient. Possibly lack of progress is linked to underlying organic problems which can be treated and/or reported to a treating physician.

In an exemplary embodiment of the invention, a first use of the chair system includes calibrating of the chair system to the patient, entering of user specific information and/or testing patient abilities. Optionally, the chair is adjustable, for example, in height, width and/or back angle. Optionally, cushions may be provided to suit certain physical deformations and/or forms. An initial set of exercises may be determined and then this set is expanded and/or changed according to progress and/or time. Optionally, one or more benchmarks are defined, for example ability to lift up a book from a table, which, once passed, rehabilitation is deemed completed (or moving to a different stage). Also, as part of gait training, once balance is sufficiently well developed, a patient may be trained only in standing position. Optionally, sitting position is retained as it allows balance training under less physical demanding conditions.

In an exemplary embodiment of the invention, the chair is used to rehabilitate a patient at least partially in water; this may require waterproof parts and/or using wireless rather than wired connections.

In an exemplary embodiment of the invention, for example for gait training, the feet of the patient rest in pedals which can move in the X-Z plane. Optionally, the pedal can also rotate (or resist or assist rotations) in the X-Z plane. Optionally, the two pedals are moved in manner which simulates walking.

Chair Variants

Some embodiments of the invention may have different designs and/or settings and/or motions. In an exemplary embodiment of the invention, seat 105 may have various shapes and slopes. Optionally the seat has a backrest. Optionally the backrest is height adjustable. Optionally the backrest tilts or moves relative to seat. Optionally the backrest has a head support. Optionally the seat and backrest may move independently or dependently. In an exemplary embodiment of the invention, the backrest is articulated with a plurality of segments, said segments capable of providing directed support to specific portions of the patient's back. Support is optionally provided in response to patient motion during exercise. In an exemplary embodiment of the invention, articulation is supported by powered joints between chair segments. Segments may be arranged, for example, vertically and/or horizontally along the chair back. In an exemplary embodiment of the invention, the powered joints include a motor for rotating a joint. An optional positional encoder may be provided for the motor in addition to or alternatively to position and/or orientation sensors for each segment. The above exemplary embodiment is optionally used to support a patient while exercising standing up or sitting down.

In an embodiment of the invention, the patient is attached to a harness suspended above the rehabilitation chair, in order to remove some body weight from the chair. Optionally, the harness is used to provide extra support to the patient during exercise. Optionally, the harness is also used as a safety device, to prevent the patient from falling to the ground during rehabilitation.

In an exemplary embodiment of the invention, the seat can be adjusted to person 104 body parameters, such as patient height and/or body weight.

In an exemplary embodiment of the invention, the rehabilitation chair is used in conjunction with foot supports. Optionally, the foot supports include sensors (e.g. pressure sensors) or attachment means, such as straps. Optionally, the foot supports can move, for example for rising the foot or rotating the foot in one or more orientations.

In an exemplary embodiment of the invention, the rehabilitation chair is used in conjunction with floor mats. Optionally, the floor mats include sensors (e.g. pressure sensors).

In an exemplary embodiment of the invention, the rehabilitation chair is used in conjunction with knee supports, which may include features such as described for the foot supports, including optionally a motor to bend the knee and/or a sensor to tell a knee position and/or enforce a knee position.

In an exemplary embodiment of the invention, the rehabilitation chair is used in conjunction with leg supports, which may include features such as described for the foot supports.

In an exemplary embodiment of the invention, the rehabilitation chair is used in conjunction with at least one arm support, which may include features such as described for the foot supports, for example using a ball mechanism based for articulation thereof in 2D or 3D and/or for rotations.

In an exemplary embodiment of the invention, a ball attachment is provided so a patient can practice kicking the ball while maintaining balance. Similarly other attachments (possibly not physically attached) are provided. Optionally, a wireless position sensor with adhesive or other attachment means is provided and which can be applied to objects of daily use, such as a book or a teakettle, so that a patient can practice with daily use objects. Optionally, the "reach-for" method is supported by a ball which is through by the system and a user must catch it. Optionally, a robotic arm is moved to a location and then moved away after a time window has elapsed, to provide similar behavior.

In an exemplary embodiment of the invention, pressure sensors are provided in one or more of a foot pad/rug, arm rest, seat cushion and seat back. Optionally, such pressure sensors indicate a pressure applied by a patient during an activity. Optionally, the sensors indicate an exact point of application of pressure (e.g., to within 5 cm), so that a point of contact of the patient can be estimated. Alternatively or additionally, fixating means is provided to link the patient's body parts to the pads. Alternatively or additionally, a position sensor on the patient's body part generates an indication of a relative location between the body part and the pressure sensor.

Optionally, the pressure sensors include torque sensors, which may be used to detect not only a degree of pressure but also a direction (in the plane of the pressure sensors) to which force is being applied.

In an exemplary embodiment of the invention, the rehabilitation chair is fitted with a manually applied brake (with optionally indicating scales). The patient optionally begins rehabilitation with high friction (i.e. more stable) and as the patient improves stability while exercising (e.g. reaching for an object) the patient then incrementally decreases the friction of the chair in order to improve strength and balance. As noted above, the stability of the chair need not be constant with angle of the chair. It can also be non-constant over the course of an exercise. For example, at first a relatively large safety zone is provided where unbalancing forces applied by a patient are ignored. After a while, the size of the zone decreases, for example based on previous performance so that the patient has to be more careful not to apply such unbalancing forces, or be prepared to correct for them.

In an exemplary embodiment of the invention, the rehabilitation chair vibrates, for example to provide massage or for feedback (e.g., that stability is about to be lost).

In some embodiments of the invention some parts can be exchanged with similar parts. For instance seat 105 may be replaced with some other types of seats, such as a bicycle seat.

Controller

In an exemplary embodiment of the invention, controller 150 controls chair 110 according to a program. Optionally or additionally the controller is a personal computer or a dedicated embedded computer. The controller controls movable parts of the chair such as chair arms 230 and/or 232, in an exemplary embodiment of the invention. The controller executes a rehabilitation method, such as described by flowchart 500 of FIG. 5. A program may be prepared in advance, and may be devised after conducting preliminary tests.

A rehabilitation method can be chosen, for instance by using a menu and a user input device. Optionally various parameters such as age and gender can be provided by a user input device.

The controller may control movements of movable part of chair 110 according to a program. For example, the controller may cause a chair seat of chair 110 to move in a way that will lift the person sitting on the chair in order to assist him standing from a sitting position.

In an exemplary embodiment of the invention, rehabilitation chair 110 has sensors or other means of measurements so there is no need to put sensors on person 104. The chair may be able to produce data of positions and/or orientations of chair parts and/or person parts. For example X axis, Y axis, and Z axis positions of person 104 for the full body and/or parts of the body. The chair may be able to produce data of other measurements such as pressure put by a human body part, or weight of person 104. Data is transferred from the rehabilitation chair 110 to the controller 150 as is illustrated by arrow 194. Data may be also transferred to a controller 150 from the data acquisition system 140, as is illustrated by arrow 192.

In an exemplary embodiment of the invention, controller 150 processes input data coming from rehabilitation chair 110, and from data acquisition 140. Optionally various user-input devices 170 are used to interact with a user. Optionally the computer outputs to output devices such as a display 160, a video unit 162, and an audio unit 164. An audio unit may be used for providing audible and/or speech instruction and/or feedback. An external connection for connection to a remote computer is optionally provided. Optionally, the controller is in communication with a network such as a LAN, WAN and/or the Internet.

In an exemplary embodiment of the invention, controller 150 performs at least one of the following tasks: it runs various programs; it controls chair 100; it controls the motion of parts of chair 110; and it transmits X-axis, and Y-axis, and Z-axis positions and rotations to chair 110.

In an exemplary embodiment of the invention, the controller controls device 110 or parts of it according to a program prepared in advance. Optionally, the controller controls multiple devices and/or rehabilitation systems. A program may be prepared after many preliminary tests. The program carries out a rehabilitation method. An operator or person 104 can choose a rehabilitation method, by using a menu and a user input device. Optionally various parameters such as age and gender can be provided using a user input device 170.

In an exemplary embodiment of the invention, patient performance is tracked over the course of the rehabilitation program. Optionally, the controller 150 performs the tracking. As the sensors 130 gather data regarding the patient and the chair, the results are stored on a database accessible to the controller 150. The controller 150 is then used to sort and process the data stored on the database.

It should be noted that some implementations of device 100 include no computer. Some implementations require no electrical power. In one example, a mechanical computer (e.g., a mechanical cam follower which guides the movement of the arm) is used to control the device parameters. Optionally, as noted above, the chair is manually operated.

Pain

In an exemplary embodiment of the invention, the chair system can detect pain, for example automatically, based on muscle tension, breathing or pulse rate, or manually, for example by user input (e.g., voice or switch). In some embodiments of the invention, an abrupt stop and/or change in exercise motion is also construed as an indicator of pain.

In an exemplary embodiment of the invention, the chair system (or other rehabilitation device, such as a robotic arm) is used to explore the range of motion and/or muscular effort at which pain occurs and the level of pain. Optionally, a patient is taught motions which will avoid the pain.

In an exemplary embodiment of the invention, rehabilitation motion trajectories are selected to take into account pain, for example, to try to expand the non-pain envelope or to limit the amount of pain in a session. Optionally, the training session is constructed to force the patient to work close to his pain threshold in order to expand his possible range of motion (and range of force) without pain. It should be noted that many activities related to balance activate a wide range of muscle and, so, are likely to cause unexpected pain. By showing the patient what these motions are (e.g., in a safe situation), the patient may be able to learn to avoid activating such muscles. Alternatively, rehabilitation may include a required dosage of activating certain muscles (e.g., so they do not atrophy), and a patient can be made aware that the amount of pain he will experience is both predetermined and required.

In an exemplary embodiment of the invention, position and other sensors are used to provide feedback if a patient moves a body part in a manner which is unnecessary and may cause pain or physical damage (e.g., for an unstable joint). Optionally, a pain warning as well as a safety warning may be supplied. Optionally the rehabilitation system prevents painful motions except where otherwise indicated, thus possibly increasing patient confidence in the system.

Balance Training

In an exemplary embodiment of the invention, a patient is rehabilitated in a chair 110, 600, or 1300. In order to improve a patient's balance, the chair is initially configured such that the ball mechanism on which the chair sits does not rotate or pivot. As the patient commences exercises and progresses through the rehabilitation schedule (performing exercises such as "go with" and "reach forward"), the chair is given an incrementally increasing range of motion. Ideally, the patient is able to maintain balance on the rehabilitation chair without assistance from the brake or chair motor. In order to determine whether it is appropriate to increase the range of motion of the chair, the patient is monitored with sensors of the type described in above and elsewhere herein.

The performance of a healthy subject can be measured using these sensors in order to determine a basal level of performance. In the alternative, a goal level of performance can be determined without regard to healthy subject testing. As the paretic patient performs exercises, the sensors measure the patient's performance. In an exemplary embodiment of the invention measurements are taken of various body parts and then the body part measurements are compared to one another in order to gauge their relative use. Optionally, multiple patient limbs and/or body parts are measured. The exercise measurements are compared against the goal performance numbers and deficiencies are noted. The rehabilitation program is then adjusted based on these deficiencies. For example, if the patient tries to stand up, a pressure sensor under each foot measures the pressure exerted by the patient. Ideally, the pressure exerted by the two feet is the same in a standing position. However, if one foot is favored, it is likely an indication that the patient needs further rehabilitation. In exemplary embodiments of the invention, the same technique is applied to exercises involving the arms and hands, or for macro-exercises, such as reaching.

In some embodiments of the invention a "reach balancing" method is used, in which a patient needs to catch or throw a small weight and/or balls. These activities require shifting one's balance. In an exemplary embodiment of the invention the balls will automatically be thrown towards the patient by a device controlled by the apparatus. As the balls near the patient, the patient is expected to reach out and try to catch the balls in the air. This type of activity typically results in the patient being off center, and therefore, it practices balance. Depending on the patient's therapeutic needs, the balls can be thrown towards the patient from specific directions. In the alternative, the patient can throw balls in specified directions in order to rehabilitate balance. Optionally, this exercise is performed while sitting down in a rehabilitation chair 110.

In some embodiments of the invention, the rehabilitation chair instigates movement to a non-balanced position and the patient is expected to correct in order to establish balance. Optionally, the arms and/or foot rests instigate movement to a non-balanced position and the patient is expected to correct in order to establish balance. Movement of the patient in terms of speed of correction, direction of corrective movement, if correction was completed, etc. can be measured by the sensors used in conjunction with the rehabilitation system. Optionally, any deficiencies in balance correction are exercised specifically.

In an exemplary embodiment of the invention, the rehabilitation system provides supplemental movement to the patient's natural movements in order to restore a balanced condition. This is achieved by sensing the position and movement of the patient, comparing these measurements to a known balanced condition and forecasting whether that balanced condition will be met, and then supplying the appropriate motive force to the chair in order to compensate for any calculated under or over correction by the patient.

In some embodiments of the invention a virtual reality (VR) type display or a television display are provided, for example to show feedback, and/or to show instructions and/or to make the activity more interesting and/or to distract person to ease his pain. A person can react to instructions and/or feedback on a screen and this can strengthen his muscles, improve balance, and improve some motions.

In some exemplary embodiments, a chair system combined with video based exercises that create the illusion of movement is used to improve balance and reduce dizziness.

In an exemplary embodiment of the invention, foot pedals are used in conjunction with the chair to simulate riding a bicycle. Sensors are used to determine if the patient is able to pedal and maintain a balanced condition.

In an exemplary embodiment of the invention, a balance exercise comprises leaning on a table (e.g., with a pressure sensitive pad) while getting up or sitting down. Uneven application of pressure may indicate a balance-related problem which can be rehabilitated. Optionally, one or more vibrational or other stimulatory patches/units may be attached to body parts and generate a stimulation prompting the patient to change his activity. Optionally, the robotic arms of the rehabilitation system provide such feedback (e.g., with a pad attachment for leaning on, rather than a handle), for example by moving or vibrating.

Another exemplary exercise is lifting a leg while remaining seated. Another exemplary exercise is standing on one foot, for example with a partially supporting chair as described below.

Leg Lifting and Back Treatment

Figure 11:
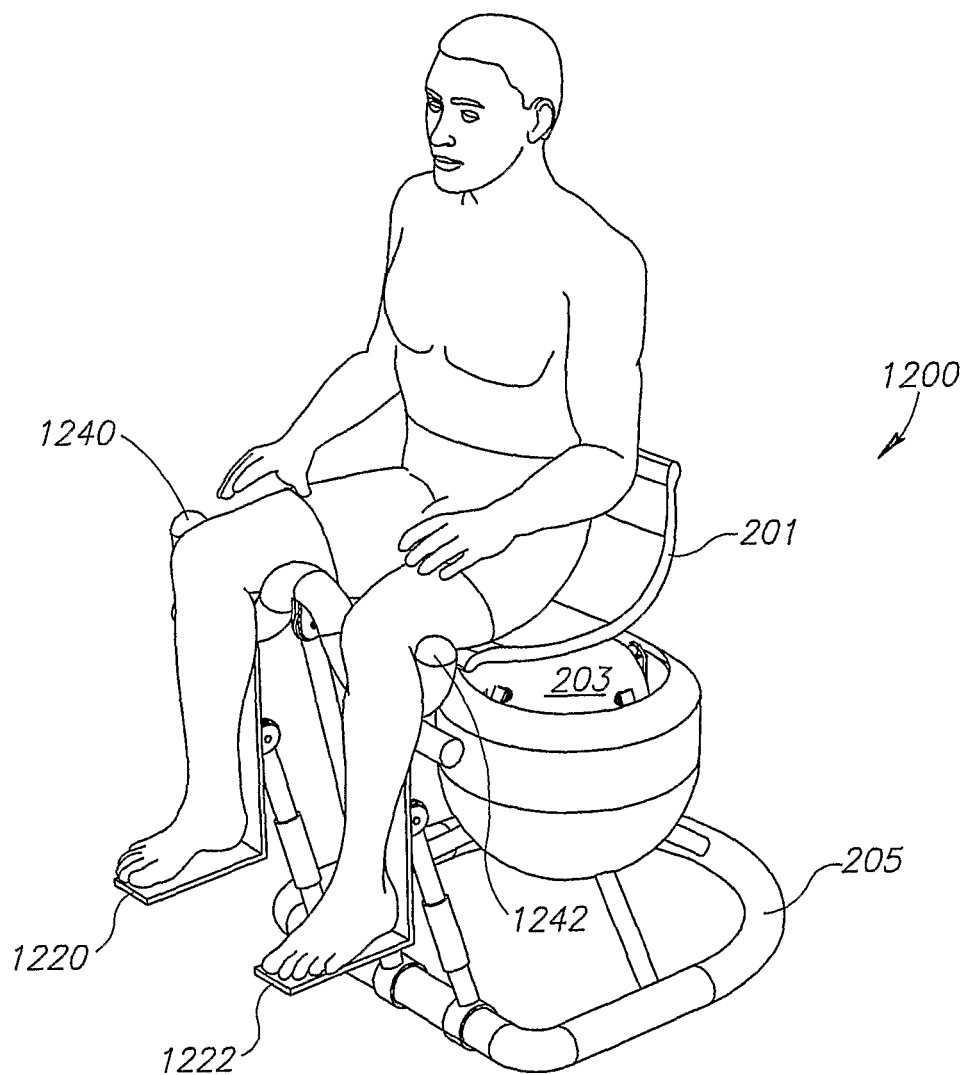
FIGS. 11 and 12 illustrate a training method and a version of rehabilitation chair, in accordance with an exemplary embodiment of the invention.
Figure 12:
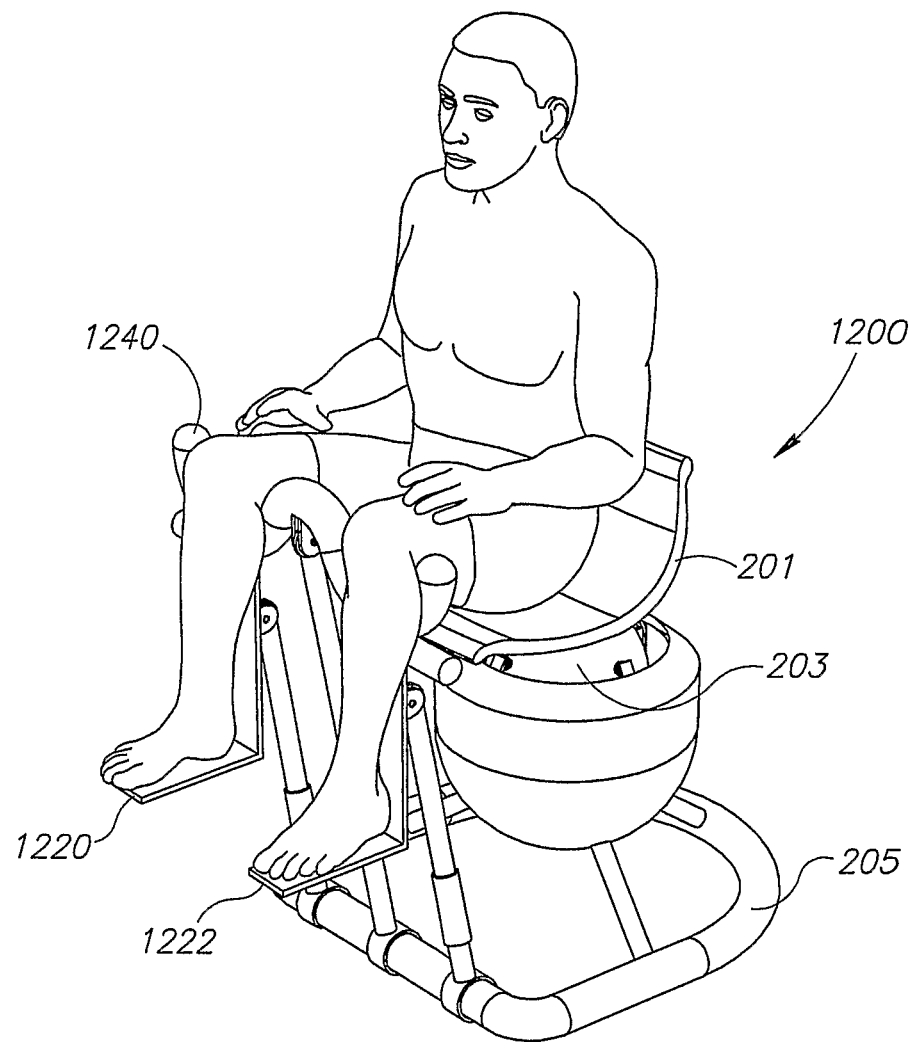

In FIGS. 11 and 12 a chair based rehabilitation device 1200 is shown, in accordance with an exemplary embodiment of the invention. Device 1200 comprises a seat 201, a base 205; a ball-based mechanism 203; foot supports 1220 and 1222; and knee support 1240 and 1242. Optionally, the knee support is one piece. Device 1200 can perform CPM of the back muscles while the patient is sitting. It can be used to improve back mobility, reduce back pain, and reduce muscle tension. Typically, treatment of the back while in a sitting position is more favorable than treatment of the back while lying down. Exercising while lying down (thus, adding more stress to the back during changing of position) can cause further back discomfort and/or injury. In an exemplary embodiment of the invention, CPM on the rehabilitation device is performed by raising and lowering the knee supports 1240, 1242, and optionally foot supports 1220, 1222, either together or separately. The raising and lowering of the supports is optionally repeated as many times and/or in as many sessions as the patient's rehabilitation requires.

In an exemplary embodiment of the invention, the various sensors are used to gauge if the CPM (or other exercise is being properly administered and/or its effect on the muscles (e.g., using EMG sensing).

Optionally, the rehabilitation chair 1200 rotates to provide exercise to the patient. The chair 1200 is capable of rotating in three dimensions around the x, y and z axes. Rotation can be achieved along one, two or all three axes in combination. In an exemplary embodiment of the invention, the knee supports 1240, 1242 and/or foot supports 1220, 1222 are in motion while the chair 1200 is rotating. Such exercise can be gentle exercise designed to move the spine and exercise back and/or stomach muscles and/or extend their range of motion. In an exemplary embodiment of the invention, such motions are used to treat pain, for example, by stretching or activating muscles which providing support to the body. Optionally, the chair includes heaters or vibrators, to help with pain.

In an exemplary embodiment of the invention, CPM exercises are accompanied with hand and arm exercises, which are optionally synchronized to the CPM. Hands and arms can be exercised by providing arm supports such as elements 1330 and 1332 shown in FIG. 13. In addition, leg motions causing spinal flexion can be non-passive, for example, assisted or against resistance.

In an exemplary embodiment of the invention, non-CPM exercises are also used to help in treating back problems. For example, the "reach forward" exercise described herein not only rehabilitates balance, but can also be used for building back strength. Optionally, non-CPM exercises are accompanied with hand and arm exercises. Hands and arms can be exercised by providing arm supports such as elements 1330 and 1332 shown in FIG. 13.

In an exemplary embodiment of the invention, chair 1200 or other chairs are used to teach correct motions to a patient, for example to avoid overstraining a muscle. In one example, a reaching action is requested from a user and the user is told during the action (e.g., using audio or speech signals) if the motion is correct and/or what is incorrect. Optionally, stimulation units are provided to specifically indicate to the patient which motion is incorrect. In another example, various typical daily motions, such as turning torso, lifting objects, reaching and/or applying forces are taught to the patient by example. Optionally, the system receives feedback form the patient if one of the motions does cause pain. In such a case, the system and/or a therapist reconfigures the "correct" motion. Correct motions might also include training in activating muscles in a certain sequence and/or refraining from applying to much strain to a muscle, joint or other body parts. All these are optionally taught, e.g., using teaching by example to the patient.

Standing Up and Sitting Down

An activity often carried out using a chair is sitting up and sitting down. As people age and/or when they suffer cognitive and/or physical damage, these tasks may become difficult. In an exemplary embodiment of the invention, a chair rehabilitation system can lead a patient through a correct trajectory of sitting down and getting up. Such leading can include, position, velocity and force feedback, also when the patient leans on various objects (such as a table or arm rests). Alternatively or additionally, the chair can provide moving parts, such as chair arms, a seat bottom and a back rest that actually move the patient along the trajectory. A pain switch is optionally provided for the patient to complain of pain. Various sitting-down and standing up exercises may be provided, for example, by moving arm rests, changing a degree of assistance of the chair and/or placing constraints on the trajectory a patient can and/or may follow.

Figure 9A:
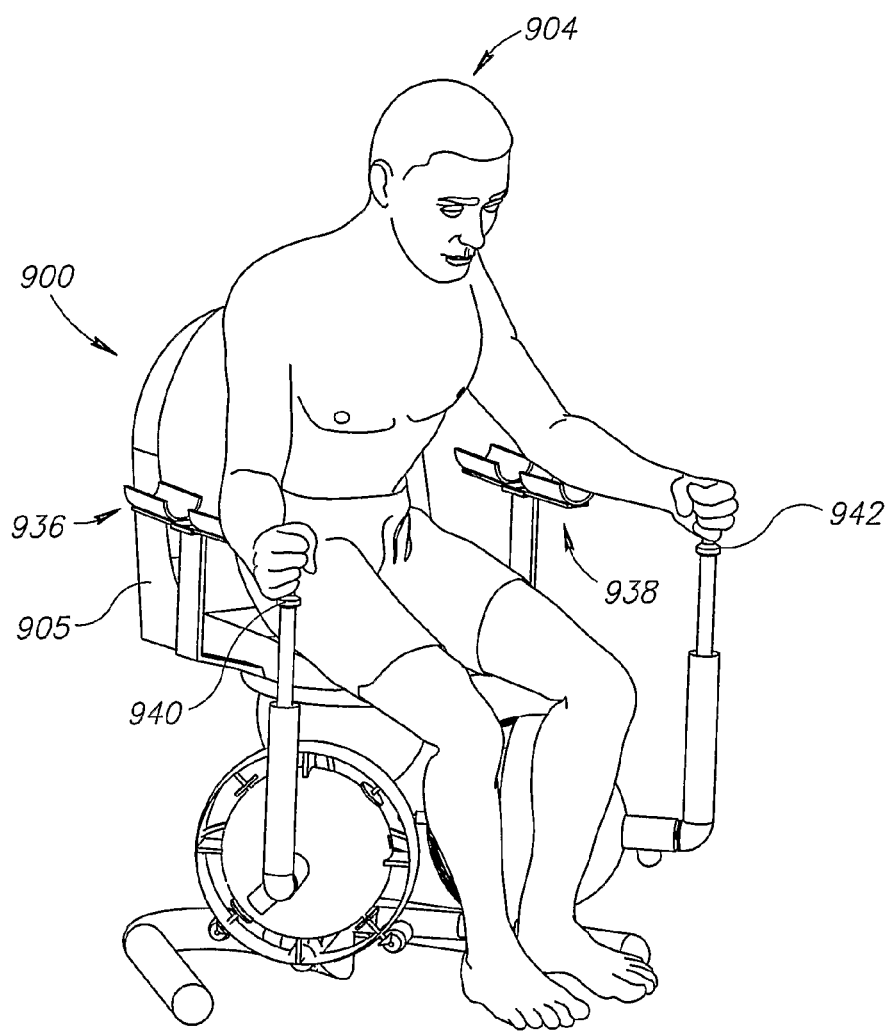
FIGS. 9A, 9B and 9C illustrate a training method and a version of rehabilitation chair, in accordance with an exemplary embodiment of the invention.
Figure 9B:
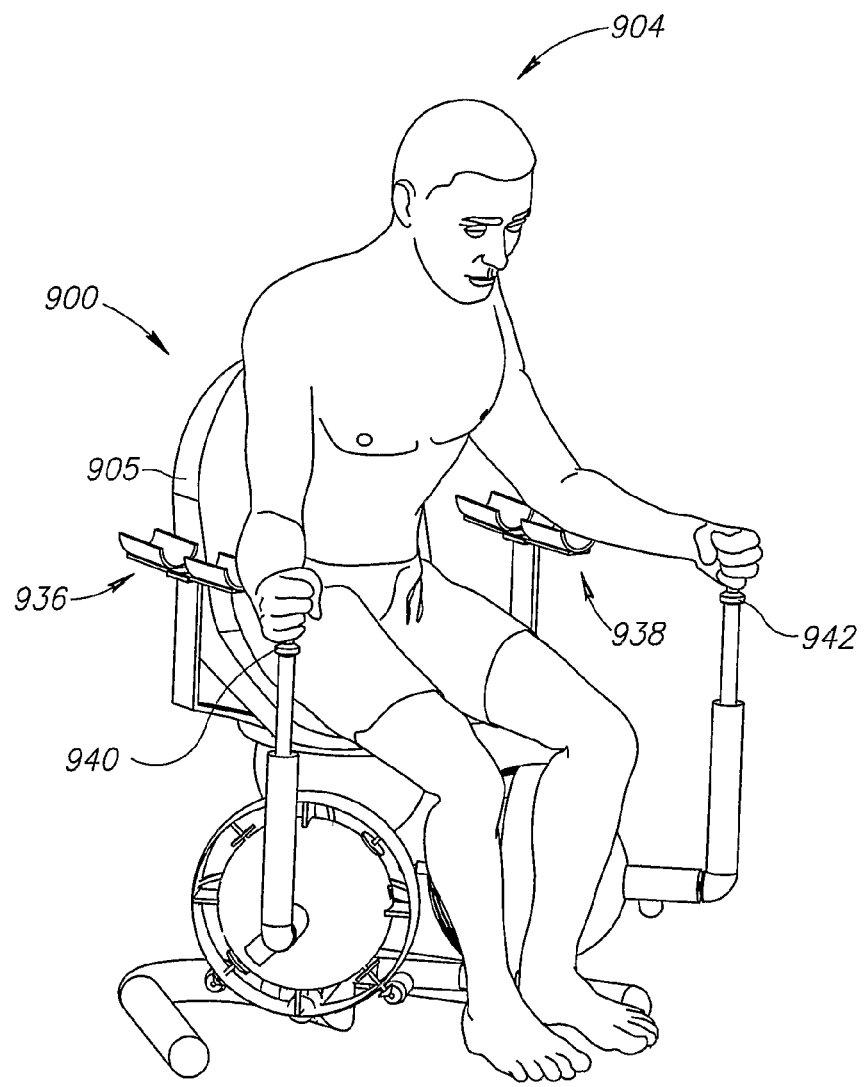
Figure 9C:
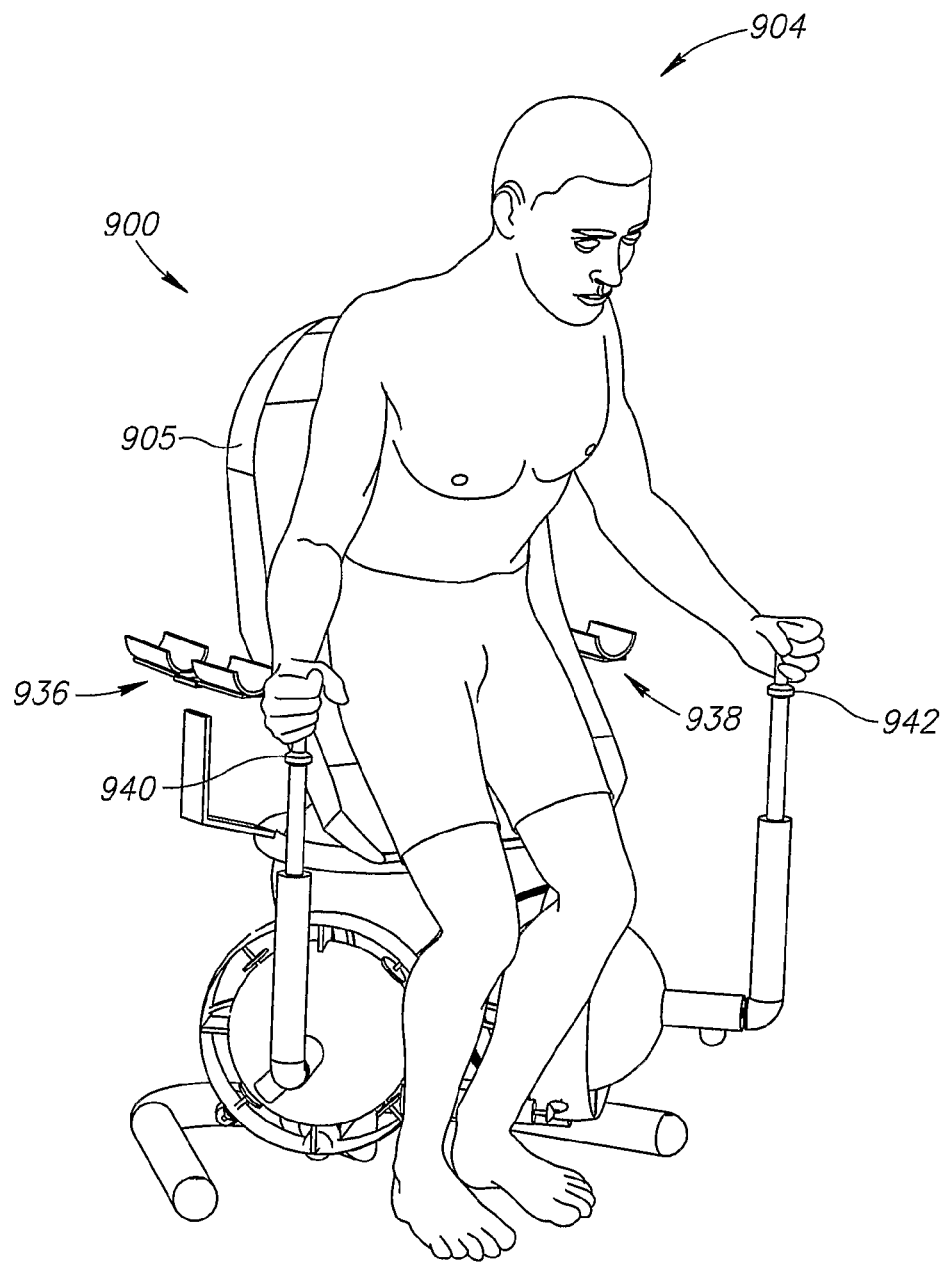

Turning now to FIG. 9A, a patient 904 is shown in a rehabilitation chair 900 in a fully seated position. In an exemplary embodiment of the invention, the patient's hands grip the chair arm tips 940 and/or 942 for support. The patient's feet are flat on the floor. The patient desires to rise from the fully seated position to a standing position. FIG. 9B illustrates how the chair 900 inclines the rear of the seat 905 to slowly bring the patient 904 up to a standing position. Optionally, the seat 905 rises in the z axis in combination with inclining the rear of the seat 905. FIG. 9C illustrates the patient standing with the feet flat on the floor, having been eased to a standing position by the seat 905. Optionally, the patient relies on the arms of the chair 936 and/or 938 for support. Optionally, the chair arms actually move the patient. Alternatively the chair arms measure force levels. Optionally, the chair arms are provided with arm rests (not shown). Optionally, the chair 900 has no chair arms. Optionally, the chair 900 has an articulated back rest, which can exert pressure on the patient 904 in order to assist the patient off the seat 905. In some embodiments of the invention, the articulated back rest is used to modify the positional relationship of the seat to the patient's back.

In an exemplary embodiment of the invention, sensors are used to monitor the status of the patient and the chair as the patient moves into a standing position. As the patient exerts force at various points, for example, the floor and/or footrests, the arms of the chair, the chair arm tips, this force is measured. Analysis of the sensor measurements is used to detect deficiencies in the patient's balance and strength and to quantify the patient's "quality of standing." These deficiencies are then rehabilitated specifically, optionally using the apparatuses and methods described herein in order to improve the quality. In an exemplary embodiment of the invention, the chair 900 is provided with a seat 905 that rotates in order to facilitate patient exercise. In an exemplary embodiment of the invention, a patient exercises by standing up and/or sitting down in a chair that rotates. Optionally, the force exerted by the patient during standing up and sitting down is measured for identification of deficiencies in ability.

A Support Chair

Figure 14A:
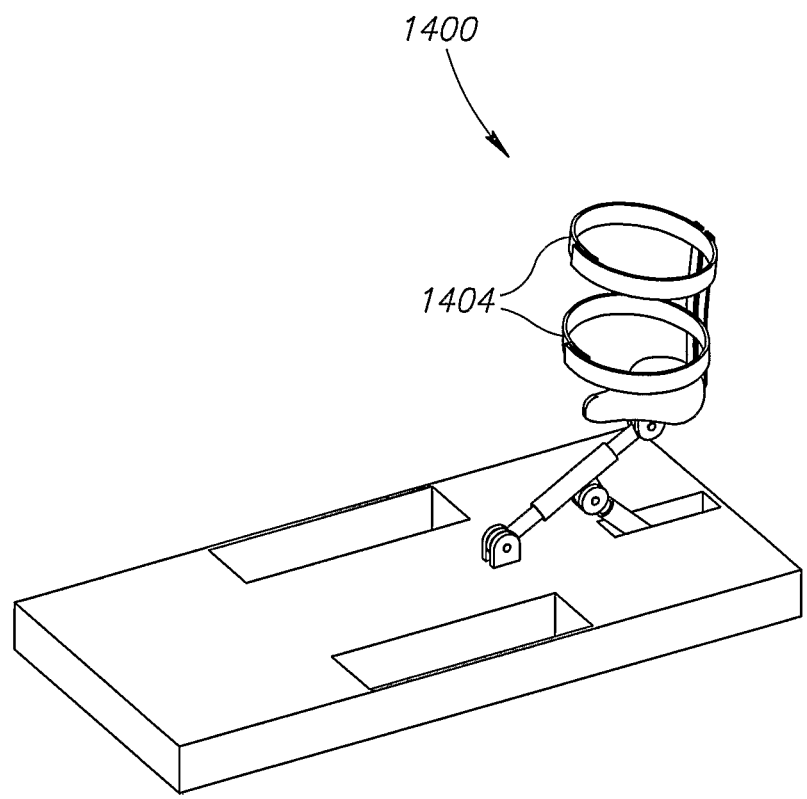
FIGS. 14A, 14B and 14C illustrate helping a person to move from sitting to standing and using a rehabilitation chair, in accordance with an exemplary embodiment of the invention.
Figure 14B:
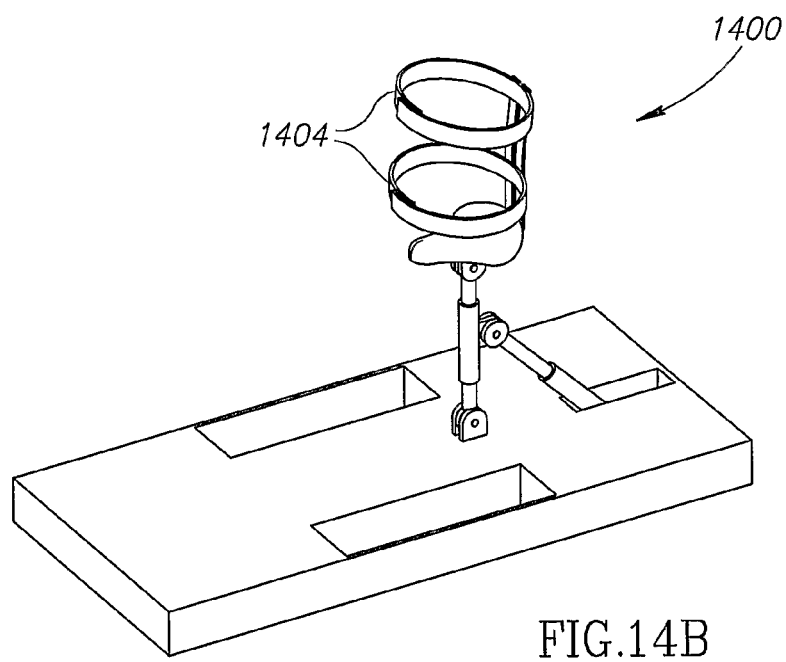
Figure 14C:
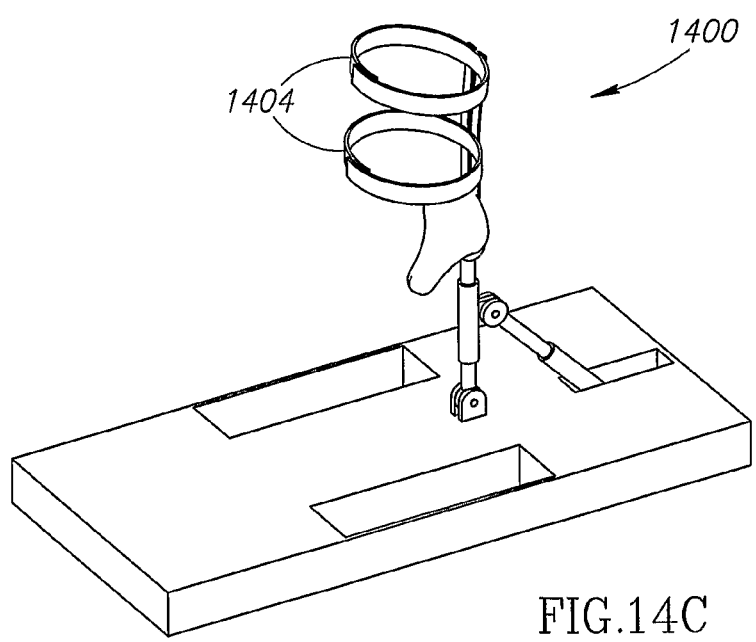

FIGS. 14A-14C illustrates a support chair 1400 in an exemplary embodiment of the invention. In FIG. 14A the chair is lowered. FIG. 14B shows the chair 1400 in a higher position than in FIG. 14A. In an exemplary embodiments of the invention, the chair 1400 moves up and down depending on the individual needs of the patient. A torso support 1404 (e.g., straps) can be optionally included with the support chair. FIG. 14C illustrates the support chair 1400 where the chair seat is in a nearly upright position where in some exemplary embodiments of the invention a patient is assisted into standing from a sitting position. Optionally, the back of the chair can bend backwards, to support a patient in a semi-prone or lying down position.

In an exemplary embodiment of the invention, a support chair is used when a patient is performing a balance activity in a semi-sitting position, with the chair providing partial support. Example exercises include kicking a ball while standing (or leaning on the chair as if it were a wall) and standing on one foot.

Training in Daily Life Activities

In an exemplary embodiment of the invention, a rehabilitation chair system is used to help rehabilitate a patient to achieve daily activities, such as eating at a table, reading a book, brushing teeth and washing dishes. In all of these activities a patient applies force away from his center of gravity potentially causing a balance problem or a problem in accurate application of force.

In use, a hand of the patient is strapped to a movable tip, for example 240, of chair system 110 and the patient attempts to or is guided through a daily activity such as picking up a fork. Optionally, the effect of the motion on the patient's balance is indicated to the patient, for example, by allowing the chair to miss-balance in slow motion. Optionally, a torso support is selectable electronically releasable and is slowly released to show the patient the effect on torso position of misbalancing while not applying correct corrective actions.

Optionally, an add-on table section with suitable sensors (e.g., contact and/or pressure) is provided. Optionally, a whiteboard for writing on is provided.

In an exemplary embodiment of the invention, device 110 is used for one or more of training a patient to do activities related to daily life, testing the patient's current ability to do such activities and/or monitoring a patient's ability.

Attachments

As noted above, some implementations of device 100 include various attachments 120. Attachments may include: medical peripherals 180 such as ECG; Cameras; a carpet, optionally provided with pressure sensors; a handle, optionally to report pain; devices to assist in various operations, such as to help a person standing; a working area such as a horizontal table; a vertical reaching target; different types of handles and grips which the person 104 holds and which are optionally connected to the rehabilitation chair at the chair arm tips 240 and 242. In some exemplary embodiments of the invention, restraints are used to immobilize selected portions of the patient's body. For example, a restraint can be used to hold a patient's arm to armrest 250 while the patient tries to flex the wrist (and thereby raise and lower the hand from a horizontal to vertical position) of that arm. Optionally, a fixed or an articulated headrest are provided. Optionally, the head rest includes means to prevent and/or encourage rotation of the head.

Safety

Chair 110 optionally includes safety means, such as, a brake, a fuse, an emergency button or switch. In an exemplary embodiment of the invention, one or more safety features are provided to prevent injury to a patient. For example, one or more of the following safety mechanism may be used:

a) Dead man switch. If a patient releases this switch (or touches a suitable button) movement of device 100 is frozen and/or all forces and resistance brought to zero. Other "safe harbor" situations can be defined instead.

b) Voice activation. Voice activation and/or deactivation may be provided, to allow a patient to shout the system to a stop.

c) Analysis. Optionally, the actual movements and/or forces applied by a patient are analyzed to determine if a threshold is being approached or if the patient is experiencing undue stress.

d) Mechanical fuse. This fuse tears or pops if a force above a certain threshold is applied to a part of the chair.

Additional Processing

In an exemplary embodiment of the invention, controller 150 generates signals indicative of forces, positions velocities and/or accelerations. Optionally, these signals are further analyzed. In one example, a biomechanical model of a body is fed with the signals, possibly indicating where a patient is deficient. In another example, analysis includes applying an FFT or other means to extract a frequency behavior of the misbalance. In some cases, such frequency behavior can indicate a source of the problem, a physical location of the problem, a cognitive source of a problem and/or suggest exercises for overcoming. For example, some types of tremor which may cause imbalance may be caused by over straining certain muscles. Even if no clear decision can be made, such information may be useful for further exploring a particular body part or ability.

Optionally, a model of the patient showing forces and/or balance problems is presented to the user and/or a therapist.

Variants

In an exemplary embodiment of the invention, the rehabilitation chair system 100 is comprised of modular parts. For example, ball mechanisms 220 and 224 are optionally interchangeable. Optionally, the rehabilitation chair can be used without chair arm rests 250 and 252.

In an exemplary embodiment of the invention, rehabilitation is performed on a platform (e.g. wobble board) instead of, or in addition to, the rehabilitation chair.

In an exemplary embodiment of the invention, the rotational abilities of the rehabilitation chair 110 are used to make the patient 104 dizzy and/or test susceptibility to dizziness. In an exemplary embodiment of the invention, the seat of the chair is moved in small arcs or in a circle. Speed may be increased over time. As the patient attempts to recover balance in the dizzy state, the patient's movements are measured by sensors and then analyzed to detect deficiencies in the patient's balance recovery abilities. Deficiencies are targeted for rehabilitation as is required in order to restore the patient's nominal balance recovery capability. Alternatively or additionally, the chair includes means for translational motion, which may also be used to cause dizziness or for other exercises. Optionally, a display showing images matching or not matching chair motions are used, to train and/or to test for dizziness susceptibility.

In an exemplary embodiment of the invention, the platform is adapted to fit under existing chairs, possibly providing a leg rest, so that rehabilitation and/or rehabilitation for balance can be provided on a standard chair. A set of cabled or wireless sensor may be provided as well. It should be noted that some of the exercises described herein may also be performed while standing up, optionally on one of many known moving platforms, while optionally providing one or more robotic arms for support, kinesthetic feedback and/or guidance. Similarly, a robotic arm module or a leg raising module may be provided in a form which can be latched on (e.g., using a strap) to an existing "standard" chair.

Training of balance and sitting down and for pain is not limited by the particular examples shown above. In particular, balance can be used, for example for supplementing the fine motor control rehabilitation methods described in U.S. Pat. App. No. 60/566,079, the disclosure of which is incorporated herein by reference. For fine motor control, balance should be maintained by the patient while applying fine motor control. Fine motor control tasks can be carried out while sitting down.

Balance rehabilitation can also be combined with neural rehabilitation. For example, U.S. Pat. App. No. 60/604,615, the disclosure of which is incorporated herein by reference uses neuronal sensing to determine when an action should be triggered. EEG signals can be used as feedback for balance-related activities.

Balance training can be used with EMG. For example, U.S. Pat. App. No. 60/566,078, the disclosure of which is incorporated herein by reference. Balance sensing can be used in addition to EMG or to determine when EMG should be delivered.

Balance training can be used with gait training, for example such as described in U.S. Pat. App. No. 60/633,428, the disclosure of which is incorporated herein by reference. In one example, sitting balance training is used prior to or as an adjunct to gait training.

Music can be used for balance training, for example such as described in U.S. Pat. App. No. 60/633,429, the disclosure of which is incorporated herein by reference. In one example, music is used to indicate balance between body sides. A channel which is too loud may be used to indicate a body portion applying too much force. Silence may be used to indicate balance, while a wobble will generate a cyclical tube and as balance is lost and alarm may increase in amplitude.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or comprises combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A rehabilitation chair system, comprising:
a seat adapted for sitting of a human thereon;
a motorized first ball mechanism attached to the seat to provide rotational movement of the seat;
at least one extender adapted to move relative to said seat using a motorized second ball mechanism;
at least one sensor which generates an indication of a balance state of said human; and
a controller configured to move the seat and said extender using the first ball mechanism and the second ball mechanism in response to the balance state measured by said at least one sensor.

2. A system according to claim 1, wherein said extender is mechanically coupled to said seat.

3. A system according to claim 1, wherein said controller moves said extender and measures a responsive change in balance state.

4. A system according to claim 1, wherein said seat is adapted to rotate out of plane of the seat.

5. A system according to claim 1 wherein said seat comprises a back.

6. A system according to claim 5, wherein said back is articulated.

7. A system according to claim 5, wherein said back rotates around a vertical axis thereof.

8. A system according to claim 1, wherein said seat is adapted to resist rotating thereof by using a brake.

9. A system according to claim 1, wherein said seat is adapted to lift under power at least 10 cm.

10. A system according to claim 1, comprising at least one leg mover adapted to lift at least one leg of the human from a floor on which the leg rests.

11. A system according to claim 10, comprising at least a second leg mover adapted to lift at least a second leg from said floor.

12. A system according to claim 11, wherein said leg movers are adapted to be locked together.

13. A system according to claim 11, wherein said leg movers are separately movable.

14. A system according to claim 1, wherein said at least one balance sensor comprises at least one pressure mat for a foot of the human.

15. A system according to claim 1, wherein said at least one sensor comprises at least one pressure sensor for an armrest of said seat.

16. A system according to claim 1, wherein said at least one sensor comprises at least one pressure sensor positioned on the seat for a buttock.

17. A system according to claim 1, wherein said at least one sensor comprises at least one pressure sensor positioned to be placed on a table near said seat.

18. A system according to claim 1, wherein said at least one sensor comprises at least two pressure sensors configured to be symmetrically positioned relative to a person sitting in the seat.

19. A system according to claim 1, wherein said at least one sensor comprises at least four spatially separated pressure sensors.

20. A system according to claim 1, wherein said controller drives said extender according to a rehabilitation plan stored within the controller.

21. A system according to claim 1, wherein said controller drives said seat according to a rehabilitation plan stored within the controller.

22. A rehabilitation system according to claim 1, further comprising:
 a leg lift mechanism adapted to lift at least one leg of a human sitting on the seat, and the controller further configured to control the lift mechanism to repeatedly lift the at least one leg of the human, such that a spine of the human is manipulated.

23. A method of controlling a rehabilitation chair system, comprising:
 providing a seat adapted for sitting a human thereon;
 rotationally moving the seat using a motorized first ball mechanism;
 moving at least one extender relative to the seat using a motorized second ball mechanism;
 generating an indication of a balance state of the human sitting on the seat using at least one sensor; and,
 configuring a controller to move the seat and the at least one extender using the first ball mechanism and the second ball mechanism while measuring the balance state using the at least one sensor and wherein said configuring includes programming the controller with a rehabilitation plan.

24. A method according to claim 23, wherein said rehabilitation plan comprises moving the at least one extender to at least partially simulate the reaching of one or more hands of the human.

25. A method according to claim 23, wherein said rehabilitation plan comprises moving the at least one extender to at least partially simulate the lifting and placing of an object.

26. A method according to claim 23, wherein said rehabilitation plan comprises a manipulation of hands extended away from the seat.

27. A method according to claim 23, wherein said rehabilitation plan comprises an interactive exercise with feedback as the complexity of the rehabilitation plan increases.

28. A method according to claim 23, wherein said generating comprises monitoring a plurality of sensors attached to a plurality of body parts.

29. A method according to claim 23, wherein generating an indication of the balance state is divided between body sides of the human while performing the rehabilitation plan.

30. A method according to claim 23, comprising monitoring the position of at least one sensor attached to an organ of the human and analyzing the position to determine an assistance of the organ to the balance state of the human.

31. A method according to claim 30, wherein at least one sensor is attached to an arm.

32. A method according to claim 30, wherein at least one sensor is attached to a torso.

33. A method according to claim 30, wherein at least one sensor is attached to a leg.

34. A method according to claim 30, wherein monitoring the position of the organ comprises monitoring movement.

35. A method according to claim 30, wherein monitoring the position of the organ comprises monitoring resistance of the organ to motion of another body part.

36. A method according to claim 23, wherein said rehabilitation plan comprises moving a body part with at least one of the seat and the at least one extender.

37. A method according to claim 23, wherein said rehabilitation plan comprises resisting the motion of a body part with at least one of the seat and the at least one extender.

38. A method according to claim 23, wherein said rehabilitation plan comprises preventing loss of balance with at least one of the seat and the at least one extender.

39. A method according to claim 23, wherein said rehabilitation plan comprises inducing loss of balance with at least one of the seat and the at least one extender.

40. A method according to claim 23, wherein at least one of the seat and the at least one extender lifts said human.

* * * * *